US012714432B2

(12) United States Patent
Teodoru

(10) Patent No.: US 12,714,432 B2
(45) Date of Patent: Aug. 25, 2026

(54) LEFT ATRIAL APPENDAGE OCCLUSION

(71) Applicant: Medtronic, Inc., Minneapolis, MN (US)

(72) Inventor: Sebastian Teodoru, Santa Ana, CA (US)

(73) Assignee: Medtronic, Inc., Minneapolis, MN (US)

( * ) Notice: Subject to any disclaimer, the term of this patent is extended or adjusted under 35 U.S.C. 154(b) by 129 days.

(21) Appl. No.: 18/615,099

(22) Filed: Mar. 25, 2024

(65) Prior Publication Data

US 2025/0017589 A1 Jan. 16, 2025

Related U.S. Application Data

(60) Provisional application No. 63/512,957, filed on Jul. 11, 2023.

(51) Int. Cl.
*A61B 17/12* (2006.01)
*A61B 17/00* (2006.01)

(52) U.S. Cl.
CPC .... *A61B 17/12122* (2013.01); *A61B 17/0057* (2013.01); *A61B 17/12136* (2013.01); *A61B 2017/00632* (2013.01)

(58) Field of Classification Search
None
See application file for complete search history.

(56) References Cited

U.S. PATENT DOCUMENTS

| | | | |
|---|---|---|---|
| 5,306,234 | A | 4/1994 | Johnson |
| 6,152,144 | A | 11/2000 | Lesh et al. |
| 6,488,689 | B1 | 12/2002 | Kaplan et al. |
| 6,689,150 | B1 | 2/2004 | Vantassel et al. |
| 6,994,092 | B2 | 2/2006 | Van Der Burg et al. |
| 7,044,134 | B2 | 5/2006 | Khairkhahan et al. |
| 7,056,294 | B2 | 6/2006 | Khairkhahan et al. |
| 7,128,073 | B1 | 10/2006 | Van Der Burg et al. |
| 7,152,605 | B2 | 12/2006 | Khairkhahan et al. |
| 7,169,164 | B2 | 1/2007 | Borillo et al. |
| 7,192,439 | B2 | 3/2007 | Khairkhahan et al. |

(Continued)

FOREIGN PATENT DOCUMENTS

| | | | |
|---|---|---|---|
| EP | 2596754 | A1 | 5/2013 |
| EP | 2609872 | A2 | 7/2013 |

(Continued)

*Primary Examiner* — Michael W Kahelin
(74) *Attorney, Agent, or Firm* — Medler Ferro Woodhouse & Mills PLLC

(57) ABSTRACT

The present application relates to an occlusion device for occluding a left atrial appendage. The device has a stem with an elongate tubular body and a central lumen that extends from a proximal end to a distal end with a proximal portion arranged at the proximal end of the stem, The proximal portion is arranged to engage with an opening of the left atrial appendage. The device includes an expandable member arranged at the distal end of the stem. The central lumen of the stem is in fluid communication with the expandable member and the expandable member is arranged to be positioned inside a left atrial appendage. The expandable member is operable to at least partially expand and displace the proximal portion in a direction towards the expandable member.

18 Claims, 10 Drawing Sheets

(56) References Cited

U.S. PATENT DOCUMENTS 7,226,458 B2 6/2007 Kaplan et al.
7,293,562 B2 11/2007 Malecki et al.
7,309,328 B2 12/2007 Kaplan et al.
7,318,829 B2 1/2008 Kaplan et al.
7,344,543 B2 3/2008 Sra
7,527,634 B2 5/2009 Zenati et al.
7,566,336 B2 7/2009 Corcoran et al.
7,597,704 B2 10/2009 Frazier et al.
7,713,282 B2 5/2010 Frazier et al.
7,722,641 B2 5/2010 Van Der Burg et al.
7,735,493 B2 6/2010 Van Der Burg et al.
7,806,846 B2 10/2010 Chanduszko et al.
7,824,397 B2 11/2010 McAuley
7,828,810 B2 11/2010 Liddicoat et al.
7,846,168 B2 12/2010 Liddicoat et al.
7,918,865 B2 4/2011 Liddicoat et al.
7,922,716 B2 4/2011 Malecki et al.
7,955,354 B2 6/2011 Figulla et al.
7,972,359 B2 7/2011 Kreidler
7,992,757 B2 8/2011 Wheeler et al.
7,998,138 B2 8/2011 McAuley
8,007,504 B2 8/2011 Zenati et al.
8,043,329 B2 10/2011 Khairkhahan et al.
8,052,715 B2 11/2011 Quinn et al.
8,080,032 B2 12/2011 Van Der Burg et al.
8,097,015 B2 1/2012 Devellian
8,100,938 B2 1/2012 Figulla et al.
8,142,470 B2 3/2012 Quinn et al.
8,197,527 B2 6/2012 Borillo et al.
8,221,445 B2 7/2012 Van Tassel et al.
8,262,694 B2 9/2012 Widomski et al.
8,287,563 B2 10/2012 Khairkhahan et al.
8,323,309 B2 12/2012 Khairkhahan et al.
8,361,111 B2 1/2013 Widomski et al.
8,460,282 B2 6/2013 McAuley
8,498,691 B2 7/2013 Moll et al.
8,523,897 B2 9/2013 Van Der Burg et al.
8,535,343 B2 9/2013 Van Der Burg et al.
8,561,872 B2 10/2013 Wheeler et al.
8,636,764 B2 1/2014 Miles et al.
8,647,350 B2 2/2014 Mohan et al.
8,647,367 B2 2/2014 Kassab et al.
8,663,245 B2 3/2014 Plott et al.
8,663,268 B2 3/2014 Quinn et al.
8,663,273 B2 3/2014 Khairkhahan et al.
8,685,055 B2 4/2014 Vantassel et al.
8,690,911 B2 4/2014 Miles et al.
8,715,302 B2 5/2014 Ibrahim et al.
8,715,318 B2 5/2014 Miles et al.
8,764,793 B2 7/2014 Lee
8,771,297 B2 7/2014 Miller et al.
8,784,469 B2 7/2014 Kassab
8,795,297 B2 8/2014 Liddicoat et al.
8,795,328 B2 8/2014 Miles et al.
8,828,051 B2 9/2014 Javois et al.
8,840,641 B2 9/2014 Miles et al.
8,845,711 B2 9/2014 Miles et al.
8,852,181 B2 10/2014 Malecki et al.
8,932,308 B2 1/2015 Ibrahim et al.
8,975,310 B2 3/2015 Savage
8,986,325 B2 3/2015 Miller et al.
9,011,551 B2 4/2015 Oral et al.
9,050,065 B2 6/2015 Whitman et al.
9,144,431 B2 9/2015 Friedman et al.
9,161,758 B2 10/2015 Figulla et al.
9,186,152 B2 11/2015 Campbell et al.
9,186,174 B2 11/2015 Krishnan
9,198,683 B2 12/2015 Friedman et al.
9,211,124 B2 12/2015 Cully et al.
9,271,736 B2 3/2016 Heipl
9,271,819 B2 3/2016 Liddicoat et al.
9,295,472 B2 3/2016 Ottma
9,351,716 B2 5/2016 Miles et al.
9,375,218 B2 6/2016 Wheeler et al.
9,408,608 B2 8/2016 Fung et al.
9,427,220 B2 8/2016 Whitman et al.
9,427,235 B2 8/2016 Krishnan
9,456,822 B2 10/2016 Krishnan
9,474,516 B2 10/2016 Clark et al.
9,486,281 B2 11/2016 Fung et al.
9,498,206 B2 11/2016 Fung et al.
9,498,223 B2 11/2016 Miller et al.
9,510,811 B2 12/2016 Akpinar
9,510,904 B2 12/2016 Krishnan
9,522,006 B2 12/2016 Liddicoat et al.
9,532,772 B2 1/2017 Moszner et al.
9,572,584 B2 2/2017 Miles et al.
9,592,110 B1 3/2017 Dan et al.
9,649,115 B2 * 5/2017 Edmiston ......... A61B 17/12022
9,650,730 B2 5/2017 Heipl et al.
9,668,671 B2 6/2017 Bruce et al.
9,693,780 B2 7/2017 Miles et al.
9,693,781 B2 7/2017 Miles et al.
9,717,488 B2 8/2017 Kassab
9,743,932 B2 8/2017 Amplatz et al.
9,750,505 B2 9/2017 Miles et al.
9,763,666 B2 9/2017 Wu et al.
9,808,253 B2 11/2017 Zhang et al.
9,839,431 B2 12/2017 Willems et al.
9,848,898 B2 12/2017 Friedman et al.
9,861,370 B2 1/2018 Clark et al.
9,883,864 B2 2/2018 Miles et al.
9,883,936 B2 2/2018 Sutton et al.
9,936,956 B2 4/2018 Fung et al.
9,943,315 B2 4/2018 Kaplan et al.
10,052,168 B2 8/2018 Krishnan
10,064,628 B2 9/2018 Edmiston et al.
10,076,337 B2 9/2018 Miles et al.
10,130,369 B2 11/2018 Fung et al.
10,143,456 B2 12/2018 Javois
10,143,475 B2 12/2018 Ibrahim et al.
10,143,478 B2 12/2018 Forbes
10,154,801 B2 12/2018 Bruce et al.
10,231,737 B2 3/2019 Amplatz et al.
10,251,650 B2 4/2019 Fung et al.
10,258,343 B2 4/2019 Zhang et al.
10,258,408 B2 4/2019 Fung et al.
10,292,710 B2 5/2019 Clark et al.
10,292,711 B2 5/2019 Olson et al.
10,307,167 B2 6/2019 De Cannier
10,314,594 B2 6/2019 De Canniere
10,327,780 B2 6/2019 Cohn et al.
10,349,935 B2 7/2019 Mohan et al.
10,349,948 B2 7/2019 Rogowski et al.
10,350,094 B2 7/2019 Fitz
10,398,488 B2 9/2019 Coulombe
10,405,866 B2 9/2019 Chakraborty et al.
10,405,919 B2 9/2019 Seiber et al.
10,420,564 B2 9/2019 Whisenant et al.
10,426,589 B2 10/2019 Van Der Burg et al.
10,499,924 B2 12/2019 Kassab
10,531,878 B2 1/2020 Giridharan et al.
10,531,943 B1 1/2020 Dan et al.
10,537,332 B2 1/2020 Edmiston et al.
10,548,579 B2 2/2020 Turkington et al.
10,582,929 B2 3/2020 Davis et al.
10,582,930 B2 3/2020 Davis et al.
10,595,861 B2 3/2020 Mohan et al.
10,603,020 B2 3/2020 Weber et al.
10,617,425 B2 4/2020 Kaplan et al.
10,624,648 B2 4/2020 Li et al.
10,631,969 B2 4/2020 Davis et al.
10,660,647 B2 5/2020 Degen et al.
10,667,896 B2 6/2020 Thomas et al.
10,695,070 B2 6/2020 Miles et al.
10,702,274 B2 7/2020 Groothuis et al.
10,709,432 B2 7/2020 Ma
10,709,454 B2 7/2020 Li et al.
10,716,571 B2 7/2020 Fung et al.
10,758,241 B1 9/2020 Lashinski et al.
10,765,416 B2 9/2020 Li
10,772,637 B2 9/2020 Miles et al.
10,779,836 B2 9/2020 Pan
10,786,302 B2 9/2020 Iaizzo et al.

(56) References Cited

U.S. PATENT DOCUMENTS 10,792,045 B2 10/2020 Wang et al.
10,799,288 B2 10/2020 Fung et al.
10,806,460 B2 10/2020 Liddicoat et al.
10,813,646 B2 10/2020 Li
10,813,647 B2 10/2020 Liu et al.
10,813,649 B2 10/2020 Javois et al.
10,820,907 B2 11/2020 Mellmann et al.
10,898,202 B2 1/2021 Slaughter et al.
10,952,741 B2 3/2021 Anderson et al.
10,959,734 B2 3/2021 Fung et al.
10,966,725 B2 4/2021 Miller et al.
11,000,289 B2 5/2021 Miles et al.
11,006,938 B2 5/2021 Coyle et al.
11,020,122 B2 6/2021 Miller et al.
11,026,690 B2 6/2021 Fung et al.
11,026,694 B2 6/2021 Wang et al.
11,026,695 B2 6/2021 Melanson et al.
11,039,822 B2 6/2021 Wang et al.
11,045,202 B2 6/2021 Amplatz et al.
11,083,492 B2 8/2021 Lin et al.
11,090,056 B2 8/2021 Horton et al.
11,109,868 B2 9/2021 Forbes
11,116,510 B2 9/2021 Melanson et al.
11,123,079 B2 9/2021 Anderson et al.
11,123,080 B2 9/2021 Lashinski et al.
11,134,934 B2 10/2021 Rafiee et al.
11,154,303 B2 10/2021 Miles et al.
11,191,546 B2 12/2021 Gong et al.
11,207,073 B2 12/2021 Clark, III et al.
11,219,462 B2 1/2022 Lashinski et al.
11,224,435 B2 1/2022 Fung et al.
11,241,237 B2 2/2022 Tischler et al.
11,241,239 B2 2/2022 Cao et al.
11,253,241 B2 2/2022 Li
11,253,262 B2 2/2022 Miles et al.
11,284,899 B2 3/2022 Ibrahim et al.
11,291,454 B2 4/2022 Chen et al.
11,317,920 B2 5/2022 Amplatz et al.
11,331,104 B2 5/2022 Inouye et al.
11,344,312 B2 5/2022 Wang et al.
11,350,944 B2 6/2022 Liddicoat et al.
11,357,512 B2 6/2022 Fishel
11,369,355 B2 6/2022 Lee
11,369,374 B2 6/2022 Wheeler et al.
11,389,167 B2 7/2022 Clark, III et al.
11,399,842 B2 8/2022 Kaplan et al.
11,399,843 B2 8/2022 Lashinski et al.
11,413,048 B2 8/2022 Anderson et al.
11,419,611 B2 8/2022 Sharma
11,426,172 B2 8/2022 Melanson et al.
11,484,320 B2 11/2022 Kangas et al.
11,484,397 B2 11/2022 Dan et al.
11,497,505 B2 11/2022 Slaughter et al.
11,534,174 B2 12/2022 Amplatz et al.
11,534,175 B2 12/2022 Hill
11,540,836 B2 1/2023 Wang et al.
11,540,837 B2 1/2023 Edmiston et al.
11,540,838 B2 1/2023 Groff et al.
11,547,417 B2 1/2023 Li et al.
11,564,692 B2 1/2023 Dasnurkar et al.
11,589,873 B2 2/2023 Adawi et al.
11,615,560 B2 3/2023 Chen et al.
2002/0111647 A1 8/2002 Khairkhahan et al.
2003/0181942 A1 9/2003 Sutton et al.
2003/0195555 A1 10/2003 Khairkhahan et al.
2003/0199923 A1 10/2003 Khairkhahan et al.
2003/0204203 A1 10/2003 Khairkhahan et al.
2003/0212432 A1 11/2003 Khairkhahan et al.
2003/0220667 A1 11/2003 Van Der Burg et al.
2004/0034366 A1 2/2004 Van Der Burg et al.
2004/0044361 A1 3/2004 Frazier et al.
2004/0215230 A1 10/2004 Frazier et al.
2004/0220610 A1 11/2004 Kreidler
2004/0230222 A1 11/2004 Van Der Burg et al.
2005/0004652 A1 1/2005 Van Der Burg et al.
2005/0038470 A1 2/2005 Van Der Burg et al.
2005/0177182 A1 8/2005 Van Der Burg et al.
2005/0192626 A1 9/2005 Widomski et al.
2005/0234543 A1 10/2005 Glaser et al.
2005/0256540 A1 11/2005 Silver et al.
2006/0020271 A1 1/2006 Stewart et al.
2006/0206148 A1 9/2006 Khairkhahan et al.
2007/0043391 A1 2/2007 Moszner et al.
2007/0060951 A1 3/2007 Shannon
2007/0083227 A1 4/2007 Van Der Burg et al.
2007/0225760 A1 9/2007 Moszner et al.
2008/0015619 A1 1/2008 Moszner et al.
2008/0033457 A1 2/2008 Plott et al.
2008/0125795 A1 5/2008 Kaplan et al.
2008/0294175 A1 11/2008 Bardsley et al.
2008/0312664 A1 12/2008 Bardsley et al.
2009/0171386 A1 7/2009 Amplatz et al.
2009/0306685 A1 12/2009 Fill
2010/0131007 A1 5/2010 Figulla et al.
2010/0191279 A1 7/2010 Kassab et al.
2010/0204716 A1 8/2010 Stewart et al.
2010/0262182 A1 10/2010 Moszner et al.
2010/0286718 A1 11/2010 Kassab et al.
2011/0054515 A1 3/2011 Bridgeman et al.
2011/0082495 A1 4/2011 Ruiz
2011/0178539 A1 7/2011 Holmes et al.
2011/0218566 A1 9/2011 Van Der Burg et al.
2011/0276075 A1 11/2011 Fung et al.
2011/0282250 A1 11/2011 Fung et al.
2011/0295060 A1 12/2011 Zenati et al.
2011/0301595 A1 12/2011 Mcauley
2012/0029553 A1 2/2012 Quinn et al.
2012/0035643 A1 2/2012 Khairkhahan et al.
2012/0065662 A1 3/2012 Van Der Burg et al.
2012/0239077 A1 9/2012 Anderson et al.
2012/0239083 A1 9/2012 Kreidler
2012/0283828 A1 11/2012 Willems et al.
2013/0012982 A1 1/2013 Khairkhahan et al.
2013/0018414 A1 1/2013 Widomski et al.
2013/0110154 A1 5/2013 Van Der Burg et al.
2013/0158645 A1 6/2013 Joergensen et al.
2013/0165965 A1 6/2013 Carlson et al.
2013/0165966 A1 6/2013 Widomski et al.
2013/0190799 A1 7/2013 Clark
2013/0237908 A1 9/2013 Clark
2013/0245369 A1 9/2013 Dal Molin
2013/0296912 A1 11/2013 Ottma
2013/0317542 A1 11/2013 Clark et al.
2013/0325140 A1 12/2013 Willems et al.
2013/0331884 A1 12/2013 Van Der Burg et al.
2013/0338686 A1 12/2013 Ruiz
2014/0005714 A1 1/2014 Quick et al.
2014/0012303 A1 1/2014 Heipl
2014/0046360 A1 2/2014 Van Der Burg et al.
2014/0081314 A1 3/2014 Zaver et al.
2014/0100596 A1 4/2014 Rudman et al.
2014/0100606 A1 4/2014 Roue et al.
2014/0107696 A1 4/2014 Borillo et al.
2014/0135817 A1 5/2014 Tischler et al.
2014/0148842 A1 5/2014 Khairkhahan et al.
2014/0194921 A1 7/2014 Akpinar
2014/0336676 A1 11/2014 Pong et al.
2015/0005704 A1 1/2015 Heisel et al.
2015/0005811 A1 1/2015 Lubock et al.
2015/0133989 A1 5/2015 Lubock et al.
2016/0074043 A1 3/2016 Friedman et al.
2016/0192911 A1 7/2016 Kassab et al.
2017/0095256 A1 4/2017 Lindgren et al.
2017/0095257 A1 4/2017 Miller et al.
2017/0119400 A1 5/2017 Amplatz et al.
2017/0172738 A1 6/2017 Kassas
2017/0181852 A1 6/2017 Kassas
2017/0196568 A1 7/2017 Gross et al.
2017/0281193 A1 10/2017 Asirvatham et al.
2017/0340336 A1 11/2017 Osypka
2018/0000490 A1 1/2018 Kaplan et al.
2018/0055496 A1 3/2018 Hou et al.
2018/0064446 A1 3/2018 Figulla et al.
2018/0132877 A1 5/2018 Friedman et al.

(56) References Cited

U.S. PATENT DOCUMENTS

2018/0206830 A1 7/2018 Khairkhahan et al.
2018/0303488 A1 10/2018 Hill
2018/0369594 A1 12/2018 Werneth et al.
2019/0015109 A1 1/2019 Li
2019/0142300 A1 5/2019 Friedman et al.
2019/0167242 A1 6/2019 Rowe et al.
2019/0175191 A1 6/2019 Min et al.
2019/0209180 A1 7/2019 Kealey et al.
2019/0247052 A1 8/2019 Narula
2019/0336136 A1 11/2019 Kassab
2019/0336137 A1 11/2019 Chakraborty et al.
2019/0336195 A1 11/2019 Coulombe
2019/0357916 A1 11/2019 Inouye et al.
2020/0008870 A1 1/2020 Gruba et al.
2020/0015827 A1 1/2020 Anderson et al.
2020/0121324 A1 4/2020 O'Halloran et al.
2020/0178981 A1* 6/2020 Anderson ........ A61B 17/12172
2020/0214714 A1 7/2020 Li et al.
2020/0253614 A1 8/2020 Melanson et al.
2020/0253708 A1 8/2020 Edmiston et al.
2020/0289128 A1 9/2020 Li et al.
2020/0337685 A1 10/2020 Ma
2020/0367903 A1 11/2020 Krivoruchko
2020/0383726 A1 12/2020 Iaizzo et al.
2021/0015491 A1 1/2021 Inouye et al.
2021/0077117 A1 3/2021 Hill
2021/0085388 A1 3/2021 Fishel
2021/0093325 A1 4/2021 Wang et al.
2021/0113212 A1 4/2021 Lashinski et al.
2021/0128163 A1 5/2021 Osypka et al.
2021/0169491 A1 6/2021 Anderson et al.
2021/0169500 A1 6/2021 Melanson et al.
2021/0205010 A1 7/2021 Fung et al.
2021/0212674 A1 7/2021 Wang et al.
2021/0236132 A1 8/2021 Seiber et al.
2021/0259670 A1 8/2021 Coyle et al.
2021/0275183 A1 9/2021 Amplatz et al.
2021/0282757 A1 9/2021 Manash et al.
2021/0298763 A1 9/2021 Stahmann et al.
2021/0330333 A1 10/2021 Gray et al.
2021/0346033 A1 11/2021 Horton et al.
2021/0353354 A1 11/2021 Schuler et al.
2021/0369283 A1 12/2021 O'Halloran et al.
2021/0378679 A1 12/2021 Amplatz et al.
2021/0393271 A1 12/2021 Melanson et al.
2021/0401418 A1 12/2021 Dang et al.
2022/0000488 A1 1/2022 Anderson et al.
2022/0022854 A1 1/2022 Lashinski et al.
2022/0031333 A1 2/2022 Zhou et al.
2022/0054117 A1 2/2022 Rafiee et al.
2022/0079600 A1 3/2022 Moriyama et al.
2022/0079667 A1 3/2022 Gabay et al.
2022/0087684 A1 3/2022 Edmiston et al.
2022/0087741 A1 3/2022 Lashinski et al.
2022/0096093 A1 3/2022 Centola
2022/0104830 A1 4/2022 Centola
2022/0117555 A1 4/2022 Werneth et al.
2022/0117608 A1 4/2022 Tischler et al.
2022/0167989 A1 6/2022 Ibrahim et al.
2022/0175390 A1 6/2022 Lee et al.
2022/0211386 A1 7/2022 Amplatz et al.
2022/0218355 A1 7/2022 Wedul et al.
2022/0240941 A1 8/2022 Lashinski et al.
2022/0249101 A1 8/2022 Min et al.
2022/0257955 A1 8/2022 Zarbatany et al.
2022/0265280 A1 8/2022 Chamorro et al.
2022/0280144 A1 9/2022 Lee
2022/0287697 A1 9/2022 Roche et al.
2022/0287713 A1 9/2022 Wheeler et al.
2022/0313270 A1 10/2022 Inouye et al.
2022/0330948 A1 10/2022 Lee et al.
2022/0338877 A1 10/2022 Natesan et al.
2022/0354472 A1 11/2022 Berger et al.
2022/0354501 A1 11/2022 Clark et al.
2022/0370079 A1* 11/2022 Harari .............. A61B 17/12122
2022/0387043 A1 12/2022 Centola
2022/0401109 A1 12/2022 Zarbatany et al.
2022/0401110 A1 12/2022 Dinges et al.
2022/0409211 A1 12/2022 Moszner
2022/0409255 A1 12/2022 Li et al.
2023/0010024 A1 1/2023 Chen et al.
2023/0031497 A1 2/2023 Sharma
2023/0032647 A1 2/2023 Kaplan et al.
2023/0033509 A1 2/2023 Lashinski et al.
2023/0048873 A1 2/2023 Onushko et al.
2023/0050254 A1 2/2023 Amplatz et al.
2023/0052812 A1 2/2023 Kangas et al.
2023/0071677 A1 3/2023 Melanson et al.
2023/0074249 A1 3/2023 Smith et al.
2023/0084301 A1 3/2023 Groff et al.
2023/0130379 A1 4/2023 Akpinar et al.
2023/0149072 A1 5/2023 O'Halloran et al.

FOREIGN PATENT DOCUMENTS

EP 2630919 A1 8/2013
EP 2716234 A1 4/2014
WO 2007054116 A1 5/2007
WO 2007054118 A1 5/2007
WO 2007140797 A1 12/2007
WO 2010130617 A1 11/2010
WO 2011161136 A1 12/2011
WO 2013034764 A2 5/2013

* cited by examiner

LEFT ATRIAL APPENDAGE OCCLUSION

CROSS-REFERENCE TO RELATED APPLICATIONS

This application claims the benefit of U.S. Provisional Patent Application Ser. No. 63/512,957, filed Jul. 11, 2023, the entire content of which is incorporated herein by reference.

FIELD OF THE INVENTION

The present invention relates to a method of occluding a left atrial appendage and an occlusion device for occluding a left atrial appendage.

BACKGROUND OF THE INVENTION

The human heart is a four chambered, muscular organ that provides blood circulation through the body during a cardiac cycle. The four main chambers include the right atrium RA and right ventricle RV which supplies the pulmonary circulation, and the left atrium LA and left ventricle LV which supplies oxygenated blood received from the lungs into systemic circulation. To ensure that blood flows in one direction through the heart, atrioventricular valves (tricuspid valves TV and mitral valves MV) are present between the junctions of the atria and the ventricles, and semi-lunar valves (pulmonary valve and aortic valve) govern the exits of the ventricles leading to the lungs and the rest of the body.

The heart also includes a left atrial appendage LAA, which is a small, car-shaped sac in the muscle wall of the left atrium LA. In normal hearts, when the heart contracts, the blood in the left atrium LA and the left atrial appendage LAA is squeezed out of the left atrium LA and into the left ventricle LV. The LAA has minimal influence on cardiac output and is generally considered to be non-functional structure in the heart.

In atrial fibrillation, an irregular heartbeat causes blood flow to slow enabling clots to form. Because the left atrial appendage LAA is a small sac or pouch, blood may collect there and form clots. The clots often cause thromboembolic complications and risk to the patient. This risk increases if the thrombus or fragments of the thrombus dislodge. If all or a portion of the thrombus flows downstream, it is highly likely that the free material will become trapped in smaller and more tortuous anatomy. This increases a patient's risk for cerebral stroke or peripheral embolism. Thus, in some cases, it may be desirable to exclude or occlude the left atrial appendage LAA such that clots do not form in the left atrial appendage LAA, and if they do, they cannot escape the left atrial appendage LAA. While medications can be taken to control blood clotting and decrease the chance of stroke, a proportion of patients cannot take such medications or follow the strict regimen necessary for continued protection.

To reduce the above-mentioned risks, it is desirable to close the left-atrial appendage to reduce the occurrence of thrombus formation and the risk of thromboembolism. The present disclosure relates to improvements in catheter-based occlusion systems for occluding or excluding the left atrial appendage.

SUMMARY OF THE INVENTION

A first aspect of the invention provides an occlusion device for occluding a left atrial appendage, the device comprising: a stem with an elongate tubular body and a central lumen that extends from a proximal end to a distal end, a proximal portion arranged at the proximal end of the stem; wherein the proximal portion is arranged to engage with an opening of the left atrial appendage, an expandable member arranged at the distal end of the stem; wherein the central lumen of the stem is in fluid communication with the expandable member and wherein the expandable member is arranged to be positioned inside a left atrial appendage; and wherein the expandable member is operable to at least partially expand and displace the proximal portion in a direction towards the expandable member.

Optionally, the expandable member is arranged to receive fluid through the central lumen of the stem so as to at least partially expand within the left atrial appendage.

Optionally, the expandable member is asymmetric, having a width greater than its height.

Optionally, the width of the expandable member is substantially oval or elliptical shaped.

Optionally, the expandable member comprises a nitinol mesh.

Optionally, the distal end of the stem extends through the expandable member and is secured to an outer surface at a distal end of the expandable member.

Optionally, the stem is in fluid communication with the expandable member through at least one aperture extending from the central lumen of the stem.

Optionally, the aperture extends perpendicularly from the central lumen.

Optionally, the stem is arranged to be positioned in a distal end of a catheter so that the distal end of the catheter extends around the stem, wherein the stem is moveable between a first position and a second position, wherein in the first position, the at least one aperture is occluded and no longer in fluid communication with the expandable member, and in a second position, the at least one aperture is in fluid communication with the expandable member.

Optionally, the stem further comprises at least one aperture at the distal end of the stem, wherein the at least one aperture is arranged to be in fluid communication with the left atrial appendage.

Optionally, the expandable member comprises at least two chambers.

Optionally, the stem is in fluid communication with each chamber through at least one respective aperture so that each chamber is arranged to be expanded separately.

Optionally, the proximal portion is dome shaped and an apex of the dome is proximal to the expandable member.

Optionally, the proximal portion comprises a bioinert polymer.

Optionally, the proximal portion is at least partially coated with a material coating.

A further aspect of the invention provides an occlusion assembly for occluding a left atrial appendage, the assembly comprising: a catheter with an elongate tubular body and a central lumen that extends from a proximal end to a distal end of the catheter, the distal end arranged to be positioned at an opening of the left atrial appendage; an occlusion device comprising a stem with an elongate tubular body and a central lumen that extends from a proximal end to a distal end, a proximal portion arranged at the proximal end of the stem; wherein the proximal portion is arranged to engage with an opening of the left atrial appendage, an expandable member arranged at the distal end of the stem; wherein the central lumen of the stem is in fluid communication with the expandable member and the expandable member is arranged to be positioned inside a left atrial appendage; and wherein the expandable member is operable to at least partially expand and displace the proximal portion in a direction towards the expandable member, wherein the occlusion device is releasably connected to the distal end of the catheter.

Optionally, the occlusion assembly further comprises a fluid source coupled to the catheter, wherein the fluid source is operable to deliver fluid to the expandable member.

Optionally, when the stem of the occlusion device further comprises at least one aperture at the distal end of the stem and wherein the at least one aperture is arranged to be in fluid communication with the left atrial appendage, and wherein the fluid source is further operable to deliver fluid into the left atrial appendage.

Optionally, the occlusion assembly further comprises a plunger with a proximal end and a distal end, wherein the proximal end of the plunger is housed in the distal end of the catheter and the distal end of the plunger is releasably connected to the proximal portion of the occlusion device, so that the occlusion device is releasably connected to the catheter through the plunger.

Optionally, the fluid is biogel.

Optionally, the biogel comprises radiopaque markers.

A further aspect of the invention provides a method of occluding a left atrial appendage, the method comprising: providing an occlusion assembly for occluding a left atrial appendage, the assembly comprising: a catheter with an elongate tubular body and a central lumen that extends from a proximal end to a distal end of the catheter, the distal end arranged to be positioned at an opening of the left atrial appendage; an occlusion device comprising a stem with an elongate tubular body and a central lumen that extends from a proximal end to a distal end, a proximal portion arranged at the proximal end of the stem; wherein the proximal portion is arranged to engage with an opening of the left atrial appendage, an expandable member arranged at the distal end of the stem; wherein the central lumen of the stem is in fluid communication with the expandable member and the expandable member is arranged to be positioned inside a left atrial appendage; and wherein the expandable member is operable to at least partially expand and displace the proximal portion in a direction towards the expandable member, wherein the occlusion device is releasably connected to the distal end of the catheter, the method comprising: positioning the distal end of the catheter with the occlusion device next to an opening of the left atrial appendage; advancing the expandable distal portion of the occlusion device into the left atrial appendage, and at least partially expanding the expandable member so as to move the proximal portion into sealing engagement with the opening of the left atrial appendage.

Optionally, the occlusion device is detached from the catheter after the proximal portion has created a seal against the opening of the left atrial appendage.

Optionally, when the occlusion assembly further comprises a fluid source coupled to the catheter such that the fluid source is operable to deliver fluid to the expandable member, wherein at least partially expanding the expandable member comprises delivering fluid into the expandable member.

Optionally, the stem is in fluid communication with the expandable member through at least one aperture extending from the central lumen of the stem, and wherein delivering fluid into the expandable member comprises:

delivering fluid through the stem of the occlusion device and through the at least one aperture extending from the central lumen of the stem and into the expandable member.

Optionally, when the stem of the occlusion device further comprises at least one aperture at the distal end of the stem and wherein the at least one aperture is arranged to be in fluid communication with the left atrial appendage, the method further comprises:

delivering fluid through the stem of the occlusion device through the at least one aperture at the distal end of the stem and into the left atrial appendage.

Optionally, the stem is further comprises a catheter, and wherein the stem is positioned in the distal end of a catheter so that the distal end of the catheter extends around the stem, and wherein the stem is moveable between a first position and a second position, wherein in the first position, the at least one aperture is occluded and no longer in fluid communication with the expandable member, and in a second position, the at least one aperture is in fluid communication with the expandable member, the method further comprises:

moving the stem into the second position before fluid is delivered to the expandable member.

Optionally, the method further comprises moving the stem into the first position after fluid is delivered to the expandable member; and delivering fluid through the at least one aperture at the distal end of the stem and into the left atrial appendage.

Optionally, the fluid is a biogel, and the method further comprises incorporating radiopaque markers into the biogel.

BRIEF DESCRIPTION OF THE DRAWINGS

Embodiments of the invention will now be described with reference to the accompanying drawings, in which.

DETAILED DESCRIPTION OF EMBODIMENT(S)

Figure 1:
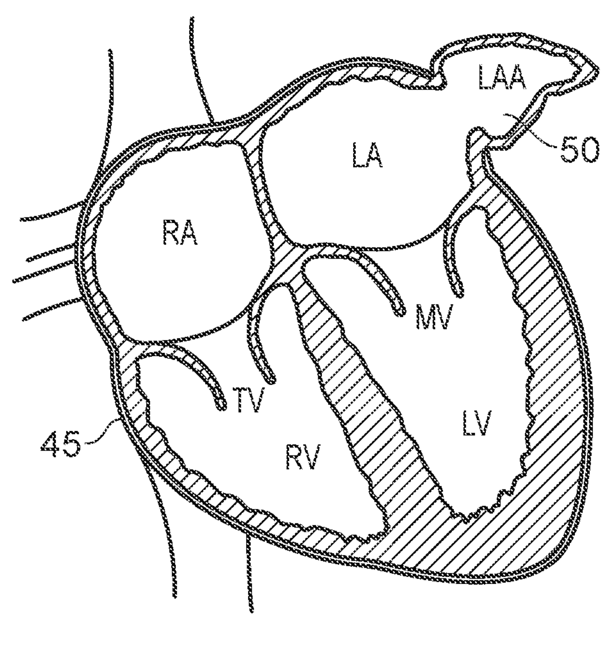
FIG. 1 is a schematic sectional illustration of a heart.

FIG. 1 is a schematic sectional illustration of a human heart 45 that depicts the four heart chambers (right atrium RA, right ventricle RV, left atrium LA, left ventricle LV) and a left atrial appendage LAA 50.

Figure 2:
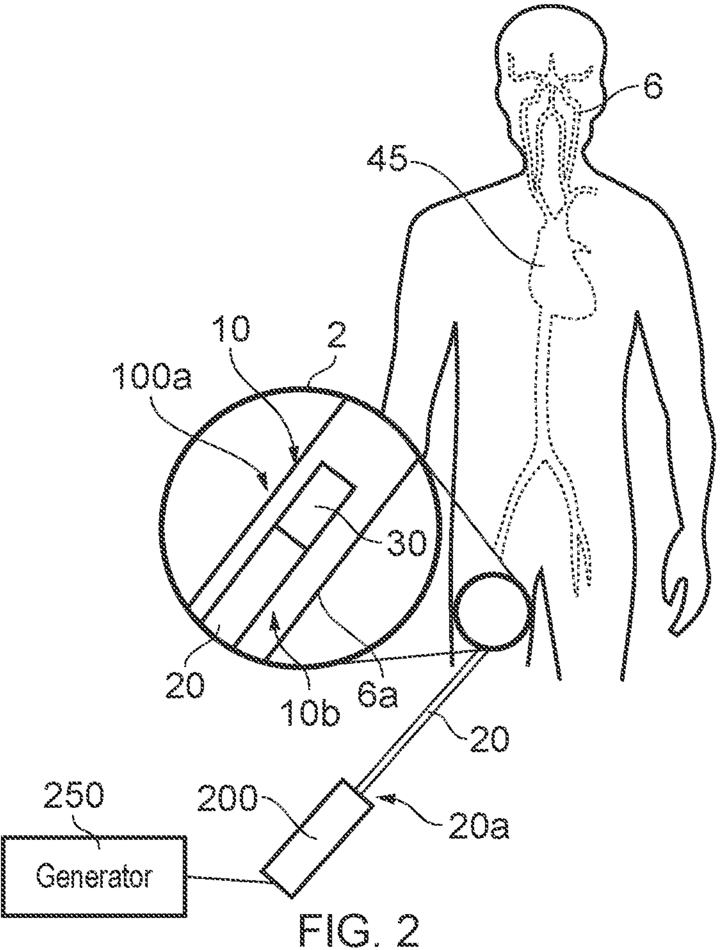
FIG. 2 illustrates a diagrammatic view of a patient undergoing a cardiovascular procedure to occlude a left atrial appendage.

FIG. 2 illustrates a diagrammatic view of a patient undergoing an exemplary left atrial appendage occlusion procedure. As indicated by the enlarged circle area 2, an occlusion assembly 10 may be inserted into a vasculature 6 of a patient, including for example, into an artery 6*a* (e.g. a femoral artery) or vein (e.g., femoral vein, internal jugular vein). The occlusion assembly 10 includes a catheter 20 and an occlusion device 100.

The catheter 20 is arranged to be positioned next to the left atrial appendage 50 within the heart 45. The catheter 20 has an elongate tubular body 22 and a central lumen 24 (shown more clearly in FIG. 5) that extends from a proximal end 20*a* of the catheter 20 to the distal end 20*b* of the catheter. As shown schematically in FIG. 2, the proximal end 20*a* of the catheter 20 is housed in a handle 200 of the occlusion device 10. The proximal end 20*a* of the catheter therefore remains outside of the patient's body while the distal portion 20*b* is advanced through the patients' vasculature 6 towards the left atrial appendage 50. A medical practitioner manipulates the position and orientation of the catheter 20 by using the handle 200. As shown, the handle 200 may also be connected to any number of systems known to those skilled in the art, generally indicated by system 250 in FIG. 2.

Figure 3:
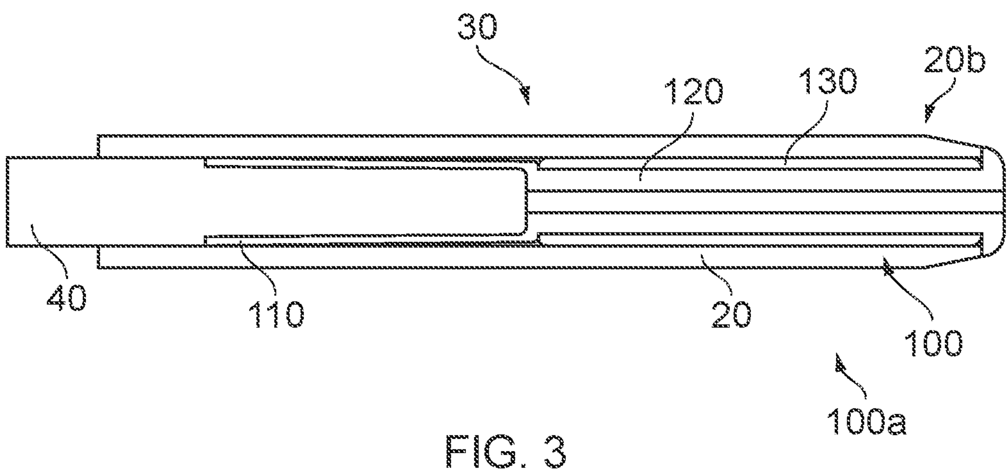
FIG. 3 illustrates an exemplary occlusion assembly.

As shown in FIGS. 2 and 3, a capsule 30 is arranged at the distal end 20*b* of the catheter 20. FIG. 3 shows a cross-sectional view of the capsule 30 and the occlusion device 100. The capsule 30 contains the occlusion device 100 in a collapsed state 100*a*. The capsule 30 protects the occlusion device 100 as the distal end 20*b* of the catheter 20 navigates through the vasculature 6 of the patient. The capsule 30 may be securely connected to the distal end 20*b* of the catheter 20 or may be formed as part of the tubular body 22 of the catheter 20 at the distal end 20*b*.

The occlusion device 100 is selectively deployable from a collapsed state 100*a* to an expanded state 100*b*. A medical practitioner may deploy the occlusion device 100 by, for example, retracting the capsule 30 towards the proximal end 20*a* of the catheter 20, or by distally pushing the occlusion device 100 from the distal end 20*b* of the catheter 20. The capsule 30 may be retracted proximally only if the capsule 30 does not form part of the tubular body 22 of the catheter 20. In these examples, when the capsule 30 is withdrawn back into the catheter 20, the proximal portion 110 of the occlusion device 100 is released to seal area 52*a* surrounding the opening 52 of the left atrial appendage. In order to proximally retract the capsule 30, the capsule 30 must be first extended away from the tubular body 22 to provide clearance between the capsule 30 and the catheter 20. In some examples. the capsule 30 may be arranged to be withdrawn back into the catheter 20 when the capsule 30 is proximally retracted. The occlusion device 100 of the occlusion assembly 10 is arranged to occlude (or obstruct) a left atrial appendage 50.

Figure 4:
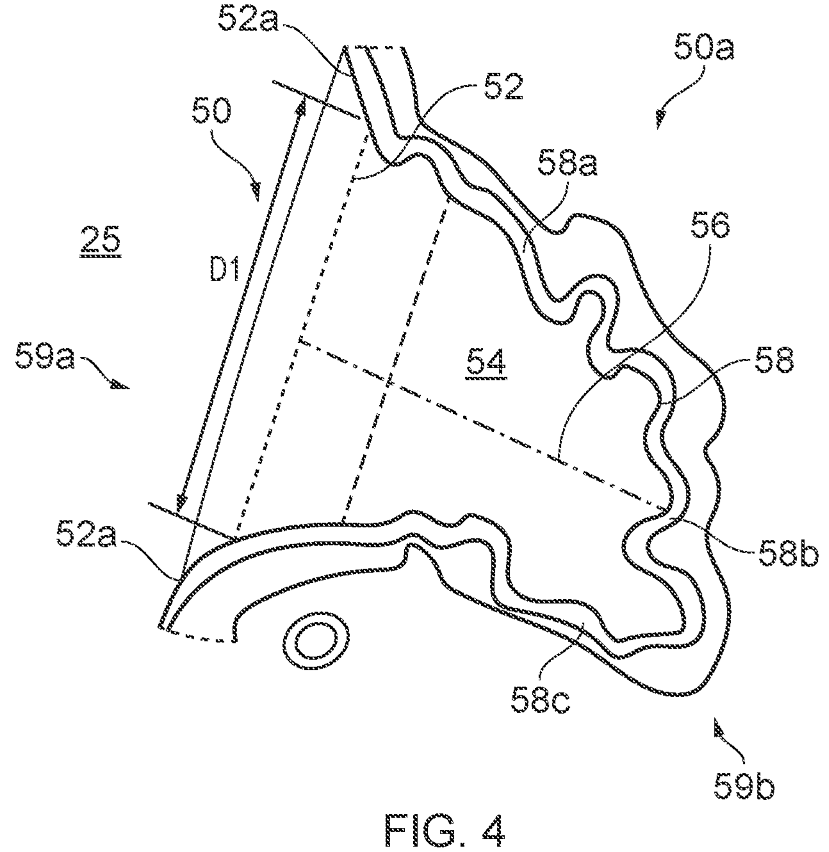
FIG. 4 illustrates an exemplary left atrial appendage.

While the shape of left atrial appendage 50 will vary for among patients, the left atrial appendage 50 is shown in FIG. 4 as being generally bursiform (pouch) shaped and has an opening 52 at a proximal end 59*a* that extends to a distal end 59*b*. The opening 52 is generally circular in shape and has a diameter D1. As shown, the opening 52 generally corresponds to the widest part of the left atrial appendage 50.

The left atrial appendage 50 has an internal volume 54 that is in fluid communication with the left atrium LA. The internal volume 54 may contain a volume of blood from the heart 45. The internal volume 54 is partially enclosed by a wall 58. As shown, the wall 58 has an irregular shape that generally forms an ear-shaped structure. In this example, the left atrial appendage wall 58 is formed of a superior wall 58*a*, an inferior wall 58*c* and a rear wall 58*b*. The left atrial appendage wall 58 includes further anterior and posterior wall sections that are not shown in FIG. 4.

The left atrial appendage 50 may have any type of morphology. For example, the left atrial appendage 50 may have a depth greater than the opening diameter D1, a smaller than the opening diameter D1, have a chicken-wing shape, cactus shape or cauliflower shape.

The left atrial appendage has a depth 56 that extends from the opening 52 (at the proximal end 59*a*) to the rear wall 58*b* (at the distal end 59*b*). Generally, the depth 56 of the left atrial appendage 50 is greatest at the rear wall 58*b*. The left atrial appendage 50 is in a natural, pre-treated state 50*a* in FIG. 4.

Figure 5:
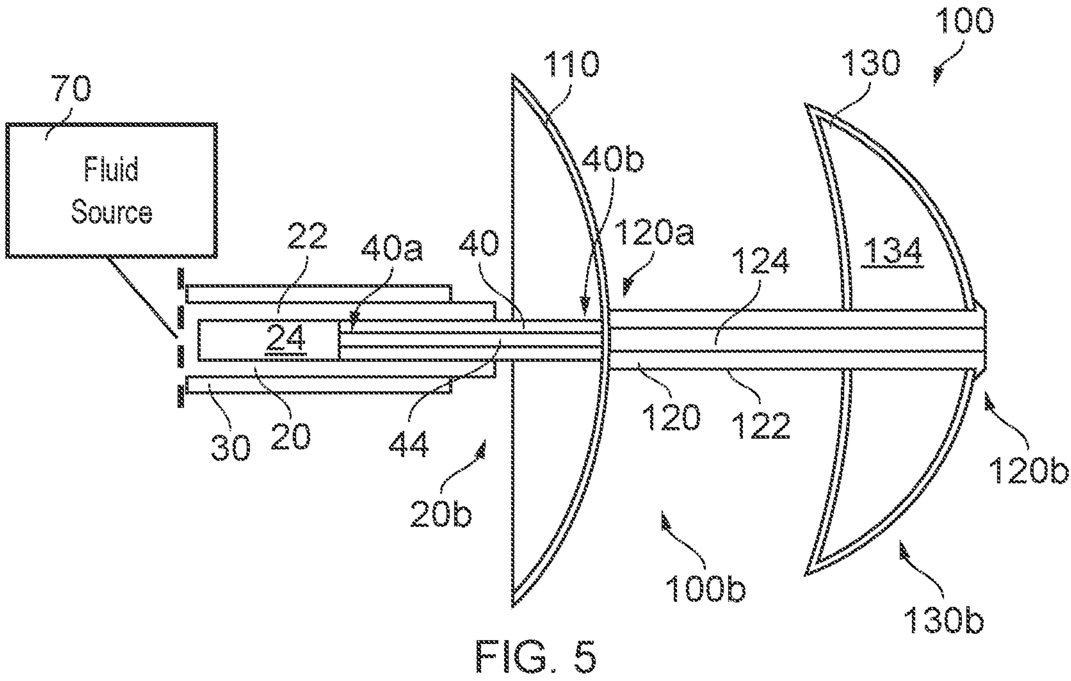
FIG. 5 illustrates an exemplary occlusion assembly with the occlusion device in an expanded state.
Figure 6A:
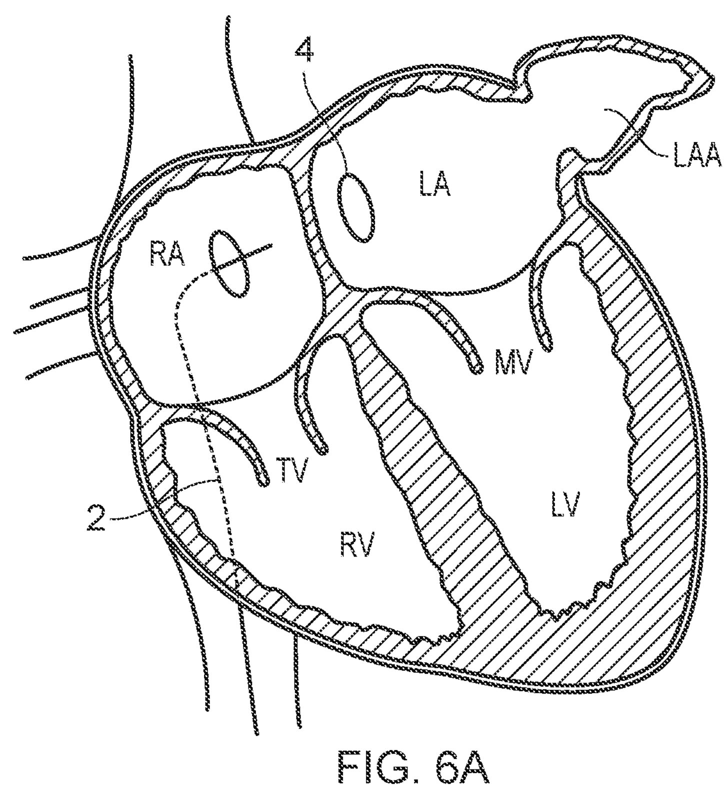
FIGS. 6A-6D are schematic views of a part of an occlusion device according to an embodiment.
Figure 6B:
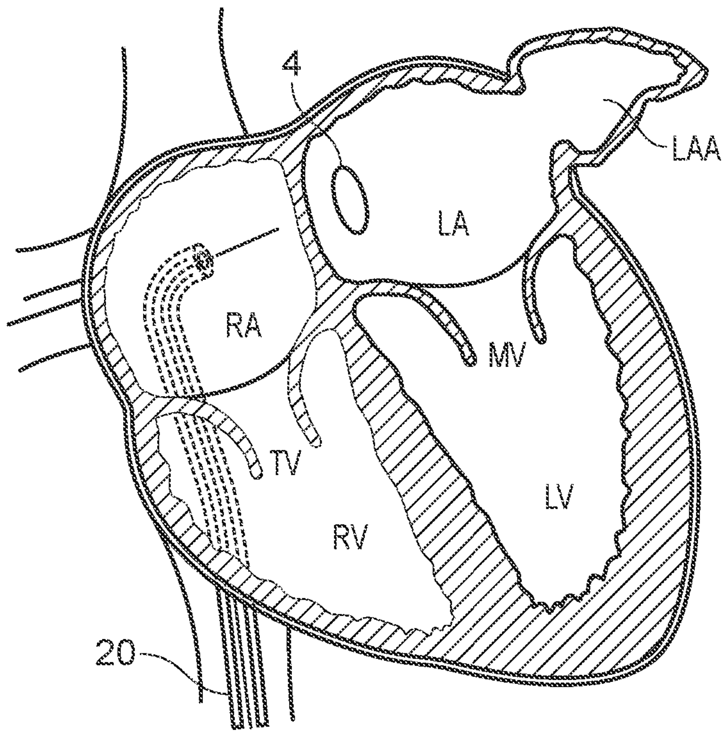
Figure 6C:
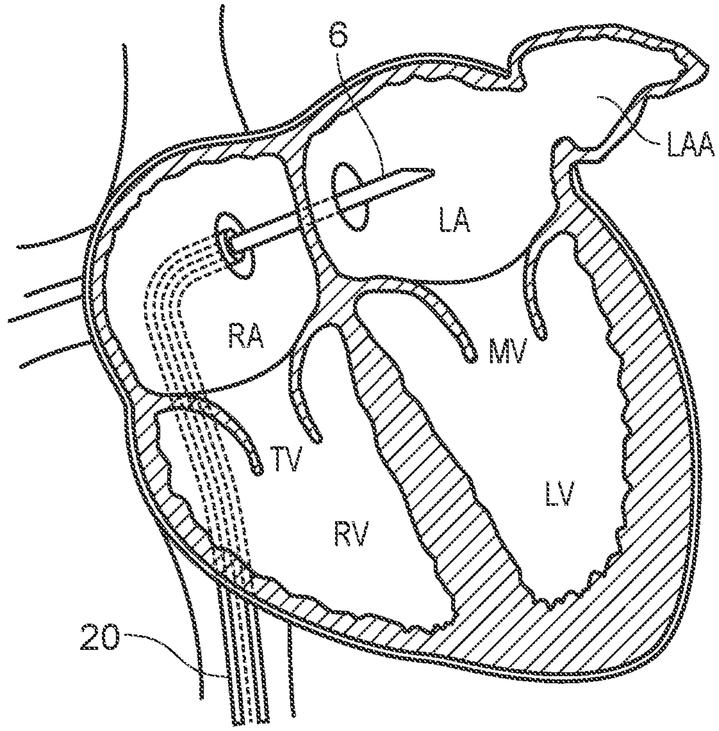
Figure 6D:
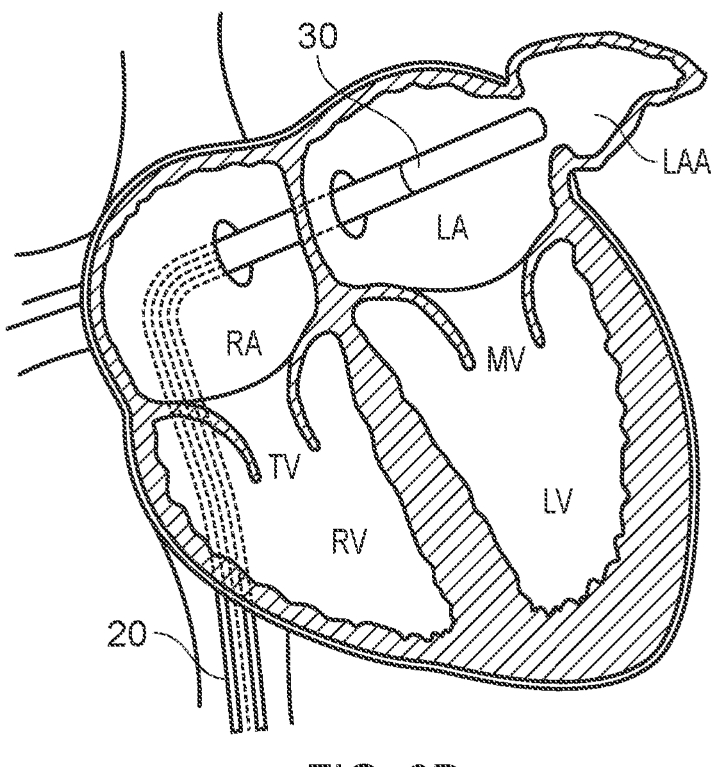

An exemplary occlusion assembly 10 for occluding a left atrial appendage 50 is shown in FIG. 5. As shown, the occlusion device 100 is in an expanded state 100*b* with the capsule 30 in a proximally retracted position. A plunger 40 is at least partially housed in the central lumen 24 of the catheter 20. The plunger 40 has a generally tubular body 42 with a central lumen 44 that extends from a proximal end 40*a* to a distal end 40*b*. The distal end 40*b* of the plunger 40 is releasably connected to a proximal portion 110 of the occlusion device 100 (discussed further below). The distal end 40*b* of the plunger 40 may be releasably connected by any suitable mechanical connection, such as a breakaway connection . . . . The plunger 40 may be selectively detached from the occlusion device 100 by the medical practitioner. The occlusion device 100 is therefore arranged to remain in the left atrial appendage 50 after being detached from the catheter 20. The central lumen 44 of the plunger 40 is in fluid communication with the central lumen 24 of the catheter 20.

Figure 7A:
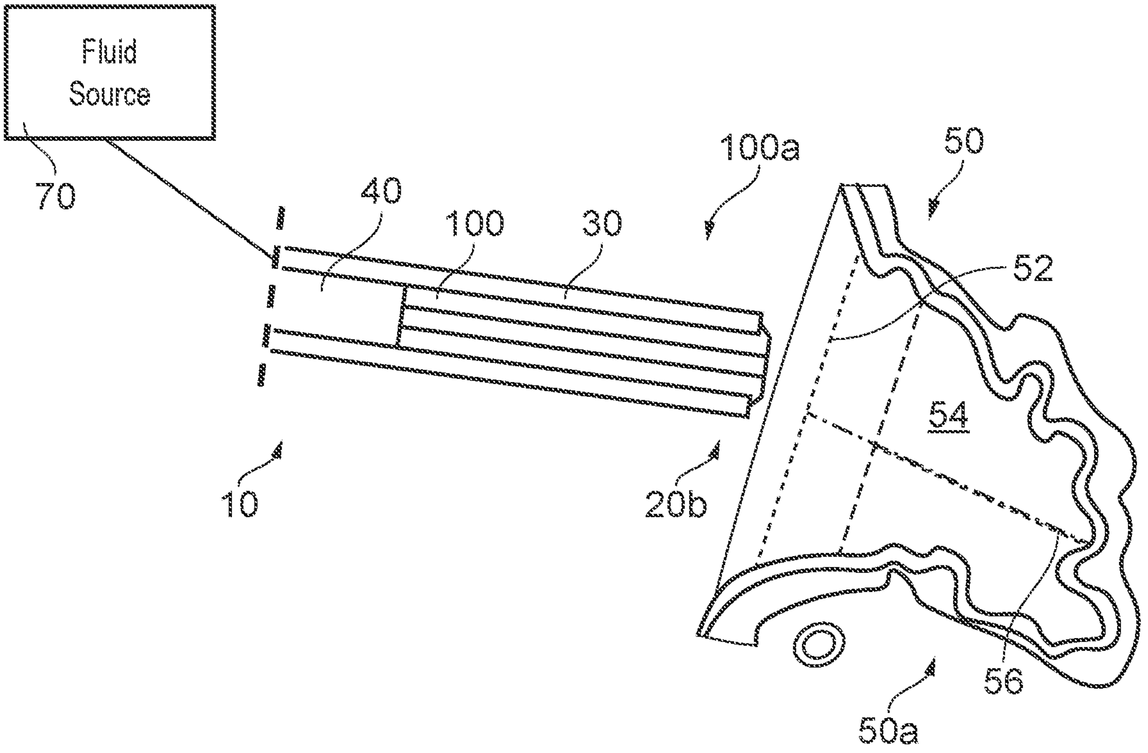
FIG. 7A illustrates a distal end of a catheter adjacent to a the left atrial appendage.

The occlusion device 100 includes a proximal portion 110, a stem 120 and a distal portion 130. As shown, the occlusion device 100 is arranged at the distal end 20*b* of the catheter 20 and is connected to the catheter 20 through the plunger 40. The occlusion device 100 is arranged to move from a collapsed state 100*a* (shown in FIGS. 3, 7A and 7B) to an inflated state 100*b* (shown in FIGS. 5, 7C and 7D). The occlusion device 100 is in a collapsed state 100*a* (i.e. not inflated) when the occlusion device 100 is housed inside the capsule 30. The occlusion device 100 is therefore in a collapsed state 100*a* as the catheter 20 is moved through the patient's vasculature 6 towards the left atrial appendage 50. As shown in FIG. 7A, the distal end 20*b* of the catheter is arranged to be positioned adjacent to the opening 52 of the left atrial appendage 50.

Referring to FIGS. 6A to 6D, a method for delivering and deploying an occlusion device to a left atrial appendage LAA will now be described. In an exemplary embodiment, a guidewire 2 is advanced after having been introduced into the vasculature via a percutaneous entry point and tracked through the vasculature into a left atrium LA of a heart. Intravascular access to the right atrium RA may be achieved via a percutaneous access site to femoral venous access up to the inferior venal cava, or other known access routes. Thereafter, a guidewire is advanced through the circulatory system, eventually arriving at the heart.

The guidewire 2 is directed into the right atrium RA (see FIG. 6A), traverses the right atrium and is made to traverse, with the aid of a pre-existing hole 4 (see FIG. 6B) or a transseptal needle 6 (see FIG. 6C) an atrial septum, thereby entering the left atrium LA. Once the guidewire 2 is positioned, the entry port and the atrial septum are dilated to permit entry of the catheter 20 into the left atrium LA towards the left atrial appendage LAA (see FIG. 6D).

There, the capsule 30 of the catheter 20 is positioned proximate the left atrial appendage LAA. Although described as a transfemoral antegrade approach for percutaneously accessing left atrium LA, the catheter 20 may be positioned within the desired area of the heart via different methods or routes. For example, and not by way of limitation, another possible path would be through the radial vein into the brachial vein, through the subclavian vein, through the superior vena cava into the right atrium, and then transeptally into the left atrium.

Yet another possible path would be through the femoral artery into the aorta (as shown in FIG. 2), through the aortic valve into the left ventricle, and then retrograde through the mitral valve into the left atrium. In another embodiment, the left ventricle LV may be accessed via a transapical approach, and the catheter 20 may be advanced through the left ventricle LV, the mitral valve, and into the left atrium LA adjacent the left atrial appendage LAA. In addition, although described with the use of a guidewire, in another embodiment hereof the catheter 20 may access the left atrium LA without the use of a guidewire.

Figure 7B:
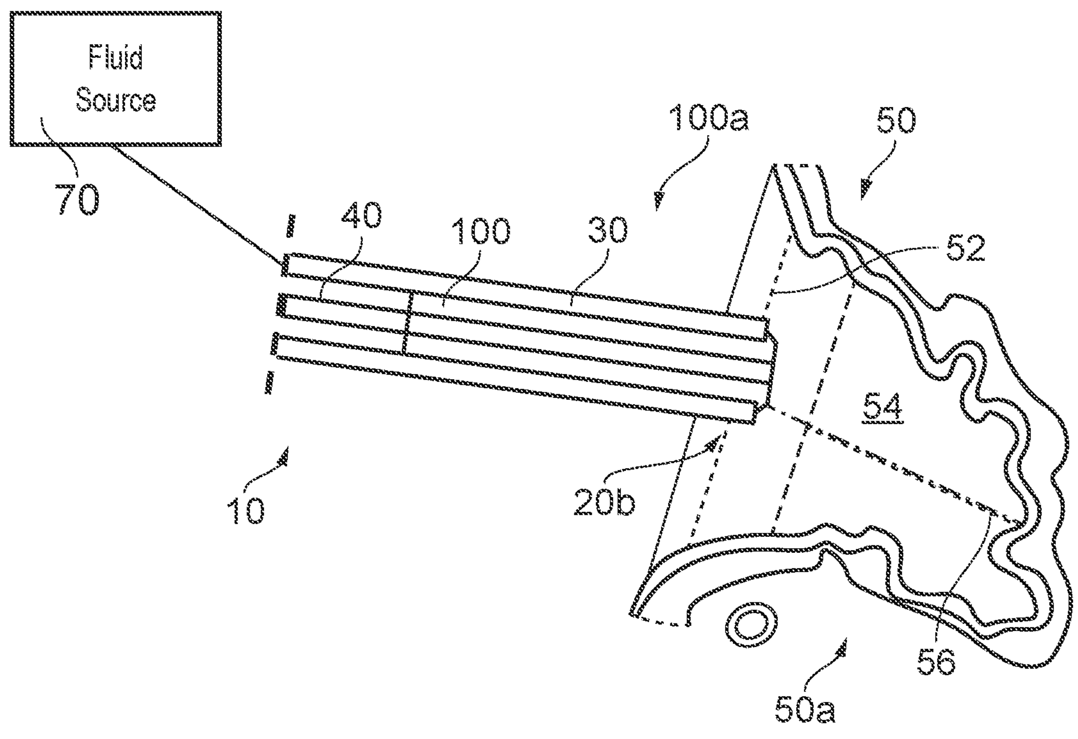
FIG. 7B illustrates a distal end of the catheter inserting into the left atrial appendage.

As shown in FIGS. 7A and 7B, which show cross-sectional views of the capsule 30, the occlusion device 100 remains in a collapsed state 100*a* when the distal end 20*b* of the catheter 20 is positioned near the opening 52 of the left atrial appendage 50. Once the distal end 20*b* of the catheter 20 is adjacent to the opening 52, the distal end 20*b* of the catheter 20 is advanced through the opening 52 and into the volume 54 of the left atrial appendage 50, as shown in FIG. 7B.

Figure 7C:
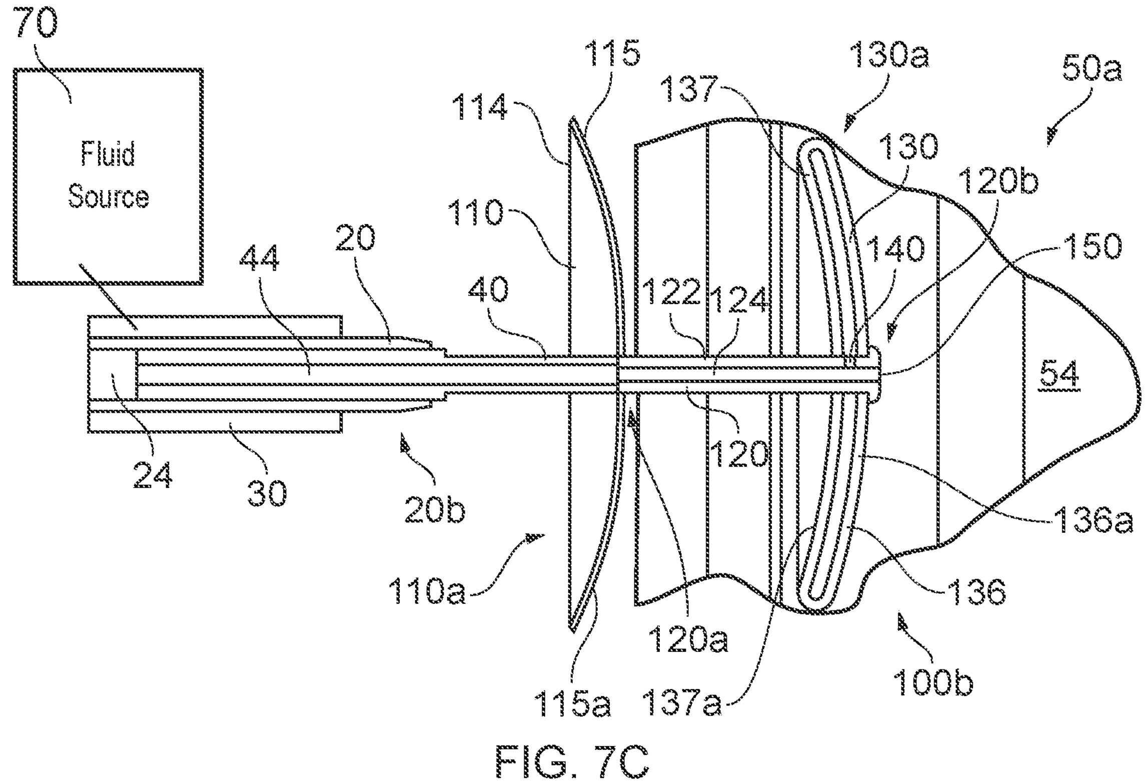
FIG. 7C illustrates the occlusion device in an expanded state in the left atrial appendage.

When the capsule 30 is proximally retracted in FIG. 7C, the occlusion device 100 deploys into an expanded state 100*b*. Preferably, the capsule 30 is retracted after the proximal end 20*b* of the catheter 20 is advanced through the opening 52 of the left atrial appendage 50 to ensure that the expandable member 130 of the occlusion device 100 is positioned inside the volume 54 of the left atrial appendage 50.

As shown, the occlusion device 100 includes a stem 120 with a substantially tubular body 122 and a central lumen 124 that extends from a proximal end 120*a* of the stem 120 to a distal end 120*b*. The proximal end 120*a* of the stem 120 is secured to the proximal portion 110 of the occlusion device 100. The proximal end 120*a* of the stem 120 may be secured to the proximal portion 110 through any suitable means, such as adhesive or any suitable mechanical engagement. The distal end 120*b* of the stem 120 is secured to an expandable member 130, which is in a collapsed configuration 130*a* in FIG. 7C. As shown more clearly in FIG. 8A, the tubular body 122 of the stem 120 passes through the expandable member 130 and is secured to an outer surface 136*a* of the distal face 136 of the expandable member 130. As shown, the distal face 136 is distal to the distal end 20*b* of the catheter 20.

The stem 120 provides fluid communication between the catheter 20 and the expandable member 130 and optionally, to the internal volume 54 of the left atrial appendage 50. The central lumen 124 of the stem 120 is in fluid communication with the central lumen 24 of the catheter 20 through the central lumen 44 of the plunger 40. The stem 120 is also in fluid communication with the expandable member 130 through an aperture 140 that extends perpendicularly from the central lumen 124 of the stem 120 (shown more clearly in FIG. 8A). In this example, only one aperture 140 extends from the central lumen 124 of the stem 120, but any number of apertures 140 may be used.

Optionally, the stem 120 may further comprise a distal aperture 150 that is arranged at the distal end 120*b* of the stem 120. The distal aperture 150 is in fluid communication with the internal volume 54 of the left atrial appendage 50, as shown more clearly in FIGS. 7C and 7D.

The expandable device 130 is arranged to move between a collapsed state 130*a* (shown in FIG. 7C) and an expanded state 130*b* (shown in FIG. 7D) after the occlusion device 100 is in a deployed state 100*b*. The expandable device 130 at least partially expands through the introduction of a fluid 170 through the aperture 140. The fluid 170 is introduced by a fluid source 70 attached to the catheter 20, and is delivered through the catheter 20, the plunger 40, through the stem 120 and into an internal volume 134 of the expandable member 130. In an expanded state 130*b*, the expandable member 130 at least partially occludes the internal volume 54 of the left atrial appendage 50.

The expandable member 130 is positioned at the distal end 120*b* of the stem 120 and is arranged to be positioned inside the left atrial appendage 50. The expandable member 130 has a width 139*a* (shown in FIG. 8A) that is arranged to extend across the width of the left atrial appendage 50 (i.e. from walls 58*a* to 58*c*) and a height 139*b* that is arranged to extend along the depth 56 of the left atrial appendage 50 (i.e. from the opening 52 to the rear wall 58*b*).

The expandable member 130 can be substantially asymmetrical. Preferably, the width 139*a* of the expandable member 130 is larger than the height 139*b*, so that the width 139*a* of the expandable member 130 can substantially extend across the width of the left atrial appendage 50. The width 139*a* of the expandable member 130 is substantially oval or elliptical shaped so that the expandable member 130 may generally conforms to the internal profile of the left atrial appendage 50. By having a larger width 139*a*, the expandable member may be easily positioned and seated inside the left atrial appendage 50 with less risk of the device migrating back out of the opening 52 and back into the heart 45. This also increases the surface area of the expandable device 130 that contacts against the left atrial appendage walls 58*a-c*. This arrangement helps prevent the occlusion device 100 from migrating back out of the left atrial appendage 50.

As shown in FIG. 7C, the expandable member 130 is arranged to be positioned and substantially extend across the widest part of the left atrial appendage 50 that is distal from the opening 52. This increases the friction between the expandable member 130 and the walls 58*a-c* of the left atrial appendage 50. This ensures that when the occlusion device 100 is in an expanded state 100*b*, the expandable member 130, although in a collapsed state 130*a*, will be less likely to migrate back through the opening 52 of the left atrial appendage 50. This also ensures that the expandable member 130 will occlude a large volume of the internal volume 54 of the left atrial appendage 50 when the expandable member 130 is at least partially expanded into an expanded state 130*b*.

The expandable member 130 has an expandable frame 135 with a distal face 136, a proximal face 137 and an internal volume 134. The expandable frame 135 may be formed of any suitable bioinert expandable material but is preferably formed of nitinol mesh. The nitinol mesh is not only compliant (and therefore may deform easily if the expandable frame 135 contacts any of the walls 58*a-c* of the left atrial appendage 50) but also expands in response to higher temperatures in the body. The expandable frame 135 therefore easily expand in the left atrial appendage 50 after the capsule 30 is retracted.

Figure 7D:
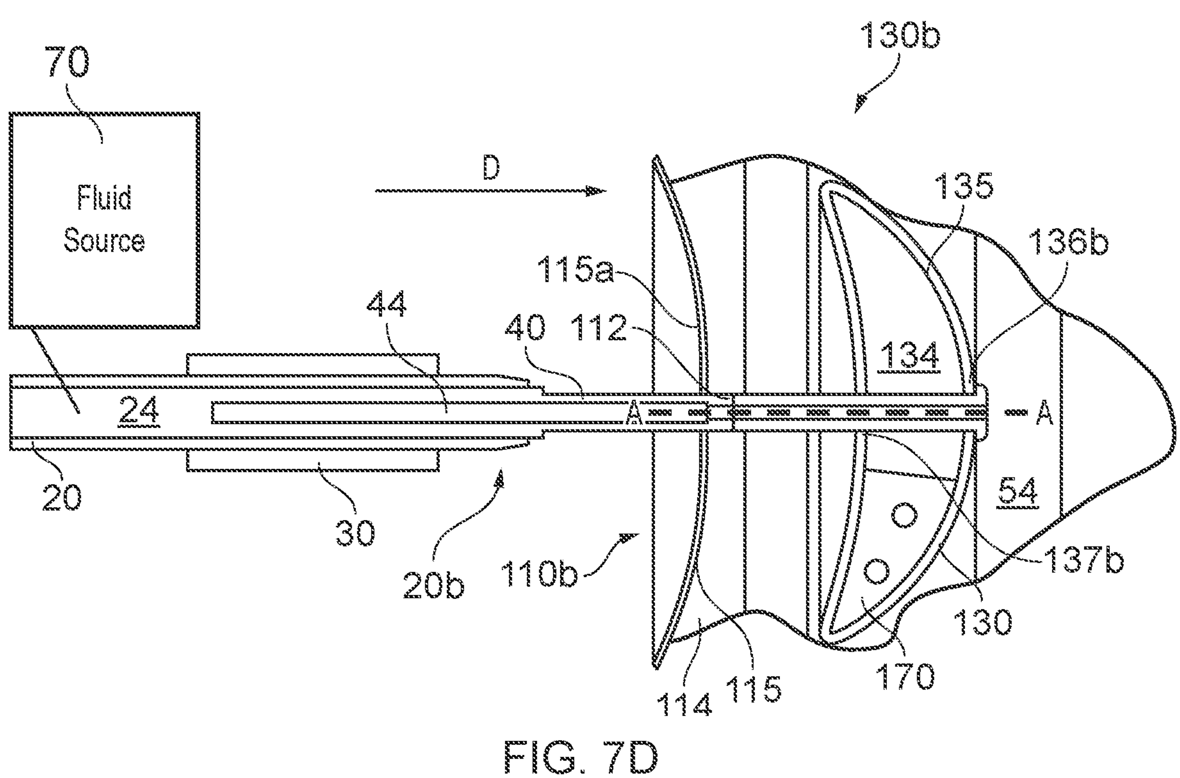
FIG. 7D illustrates the occlusion device with an expanded expandable member in the left atrial appendage.

The distal face 136 of the expandable member 130 has a distal outer surface 136*a* and the proximal face 137 of the expandable member 130 has a proximal outer surface 137*a*. Preferably, the distal outer surface 136*a* is generally dome-shaped with an apex 136*b*. As shown in FIG. 7D, the apex 136*b* of the distal outer surface 136 is distal from the distal end 20*b* of the catheter 20. Similarly, the proximal outer surface 137*a* is substantially domed with an apex 137*b*. The stem 120 is arranged to extend through the expandable member 130 through both apexes 136*b*, 137*b*.

The proximal end 120*a* of the stem 120 is connected to a proximal portion 110. As shown in FIG. 7C, the proximal portion 110 is generally dome shaped, with a rim 114 that extends around a cup portion 115. The cup portion 115 has an outer surface 115*a* and has an apex 112. The rim 114 of the proximal portion 110, in a collapsed state, is proximal to the distal end 20*b* of the catheter 20, while the apex 112 of the proximal portion 110 is distal to the distal end 20*b* of the catheter 20. The cup portion 115 is substantially circular to conform with the opening 52 of the left atrial appendage 50.

The proximal portion 110 is arranged to be brought into sealing engagement against the opening 52 of the left atrial appendage (discussed further below). The proximal portion 110 is pre-engaged configuration 110*a* in FIG. 7C, while FIG. 7D shows the proximal portion 110 in an engaged configuration 110*b* (i.e. sealing the opening 52 of the left atrial appendage 50). The proximal portion 110 has a width 119*a* that is arranged to extend across the width of the opening 52 of the left atrial appendage 50 and a height 119*b* that is arranged to extend into the left atrial appendage 50 through the opening 52. The outer surface 115*a* of the proximal portion 110 is arranged to contact against an area 52*a* surrounding the opening 52 to seal the opening 50. Preferably, the rim 114 of the proximal portion 110 is larger than the opening 52 so that the outer surface 115*a* of the proximal portion 110 contacts most of the area 52*a* surrounding the opening 52.

In this example, the proximal portion 110 is substantially circular with an apex 112. The substantially dome shape of the proximal portion 110 increases the sealing effect against the opening 52 of the left atrial appendage 50 as the proximal portion 110 provides a suctioning effect against the opening 52. However, in other examples, the proximal portion 110 may be oval, elliptical or any other suitable shape to conform to the openings 52*a* of the left atrial appendage 50. The appropriate shape and size of the proximal portion 110 may be determined by the medical practitioner using any suitable technique, such as injecting dye or radio imaging techniques. The size of the proximal portion 110 and the expandable member 130 may therefore be adjusted depending on the morphology of the left atrial appendage 50 of the patient. The proximal portion 110 seals the opening 52 of the left atrial appendage 50 to prevent any material, such as blood or clots from exiting or entering the left atrial appendage 50. The proximal portion 110 also acts as a plug that helps secure the occlusion device 100 in the left atrial appendage 50 to prevent migration of the occlusion device 100.

The proximal portion 110 is arranged to contact against the tissue forming the area 52*a* surrounding the opening 52 of the left atrial appendage 50 for extended periods of time. Therefore, at least the outer surface 115*a* of the proximal portion is formed from a bioinert polymer, such as PDMS. This is to ensure that the proximal portion 110 does not cause an inflammatory response in the area 52*a* surrounding the opening 52. The proximal portion 110 may also be partially coated with a material coating such as PLGA (poly(lactic-co-glycolic acid)). The outer surface 115*a* of the cup portion 115 may be treated with oxygen plasma to increase surface adhesion to the PLGA material. The PLGA material coating may also be used to help secure adhesion of the cup portion 115 to the area 52*a* surrounding the opening 52 of the left atrial appendage 50.

The proximal portion 110 is arranged to be brought into sealing engagement with the opening 52 of the left atrial appendage 50 as the expandable member 130 is expanded. As described above, the expandable member 130 is arranged to at least partially expand by receiving fluid 170 from a fluid source 70 through the aperture 140 of the stem 120. The fluid source 70 is in fluid communication with the central lumen 24 of the catheter 20. Therefore, the fluid source 70 is operable to deliver fluid 170 through the plunger 40 and the stem 120 to the internal volume 134 of the expandable member 130.

The expandable member 130 is arranged to expand as the fluid 170 enters into the internal volume 134 of the expandable member 130. The fluid 170 is preferably any suitable inert fluid, such as biogel, saline or contrast media. The fluid 170 is used to expand the expandable member 130 to occlude the left atrial appendage 50 and also helps maintain the expandable member 130 in the expanded state 130*b*. The fluid 170 may include radiopaque markers 170*a* so that the injection and delivery of fluid into the expandable member 130 may be observed by the medical practitioner through additional imaging techniques, such as fluoroscopy. The radiopaque markers 170*a* therefore help the medical practitioner to ensure that the occlusion device 100 is positioned correctly in the left atrial appendage 50. The radiopaque markers 170*a* also help guide the medical practitioner in providing the correct amount of fluid 170 into the expandable device 130 depending on the size of the left atrial appendage 50, which can vary depending on the morphology of the patient.

As the expandable member 130 is asymmetrical, the expandable member 130 does not evenly expand in the left atrial appendage 50, i.e. the distal face 136 and the proximal face 137 of the expandable frame 135 do not displace equally or at the same rate. Generally, the distal face 136 of the expandable member 130 is displaced further towards the distal end 59*b* of the left atrial appendage 50 than the proximal face 137. As the distal end 120*b* of the stem 120 is secured to the distal outer surface 136*a* of the expandable member 130, the expandable member 130 displaces the stem 120 as the expandable member 130 is filled with fluid 170.

As shown in FIG. 7D, the stem 120 is displaced in a direction D towards the distal end 59*b* of the left atrial appendage 50. The proximal portion 110 of the occlusion device is also displaced in a direction D as the expandable member 130 expands because the proximal end 120*a* of the stem 120 is secured to the proximal portion 110. The proximal portion 110 is therefore brought into sealing engagement against the opening 52 of the left atrial appendage 50 as the expandable member 130 is filled with fluid 170. Expanding the expandable member 130 occludes the internal volume 54 of the left atrial appendage 50 and simultaneously seals the opening 52 of the left atrial appendage 50 with the proximal portion 110. The occlusion assembly 10 therefore allows the medical practitioner to occlude and seal the left atrial appendage 50 in one procedural step without additional devices or equipment.

Figure 7E:
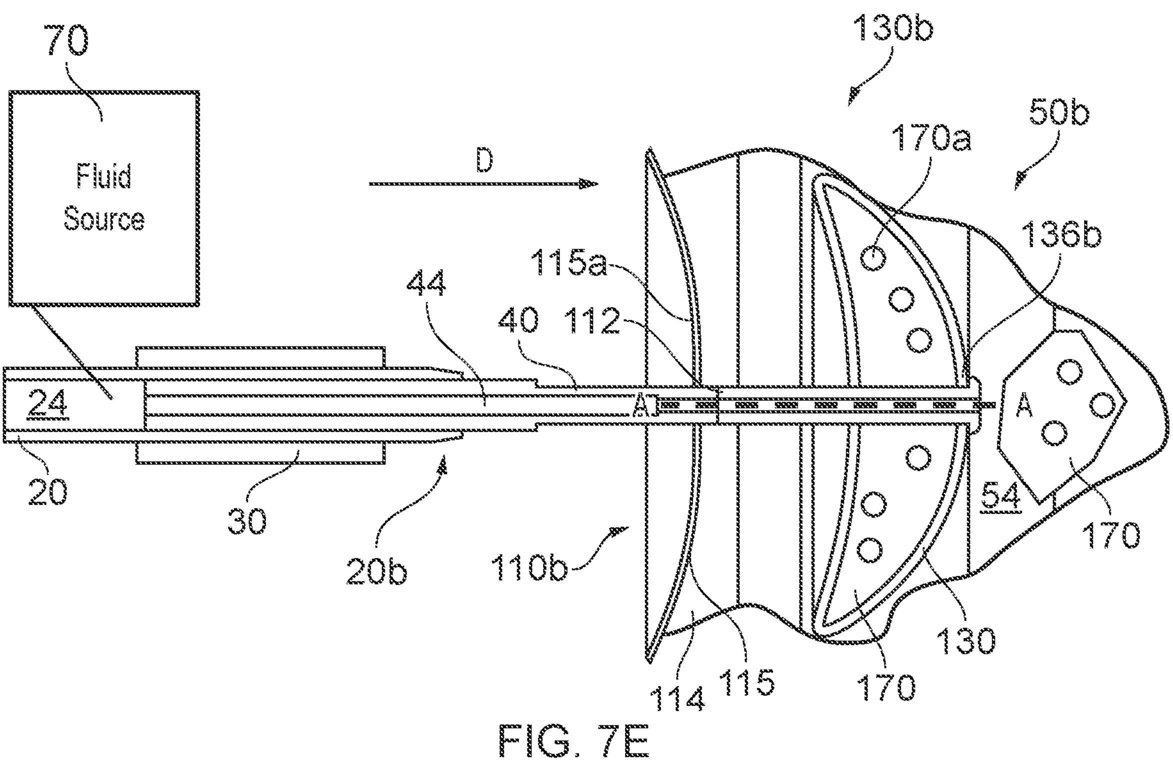
FIG. 7E illustrates the catheter detached from the occlusion device.

The occlusion device 100 is arranged to be left implanted in the left atrial appendage 50 after the expandable member 130 has been sufficiently expanded and the proximal portion 110 is brought into scaling engagement against the opening 50 of the left atrial appendage 50. The plunger 40 is releasably connected to the proximal portion 110 of the occlusion device 110 by any suitable means, such as a mechanical snap feature or a threaded arrangement. The plunger 40 may be detached by the medical practitioner by mechanically snapping the plunger 40 from the proximal portion 110, or by disengaging the threaded arrangement. After the distal end 40*b* of the plunger 40 is detached, the plunger 40 is retracted proximally into the distal end 20*b* of the catheter 20 before the catheter 20 is withdrawn from the patient. The occlusion device 100 remains in the left atrial appendage 50. FIG. 7E shows the left atrial appendage 50 in an occluded state 50*b*.

The stem 120 may have a further distal aperture 150 at the distal end 120*b* of stem 120. As shown in FIG. 7C, the distal aperture 150 is in fluid communication with the internal volume 54 of the left atrial appendage 50. After the expandable member 130 has been expanded into an expanded state 130*b*, the fluid source 70 may be used to deliver fluid 170 into the remaining internal volume 54 of the left atrial appendage 50. The fluid 70 may be delivered to occlude the remaining volume of the left atrial appendage 50 or to help secure the occlusion device 100 in place and prevent migration of the occlusion device 100.

Figures 8A, 8B:
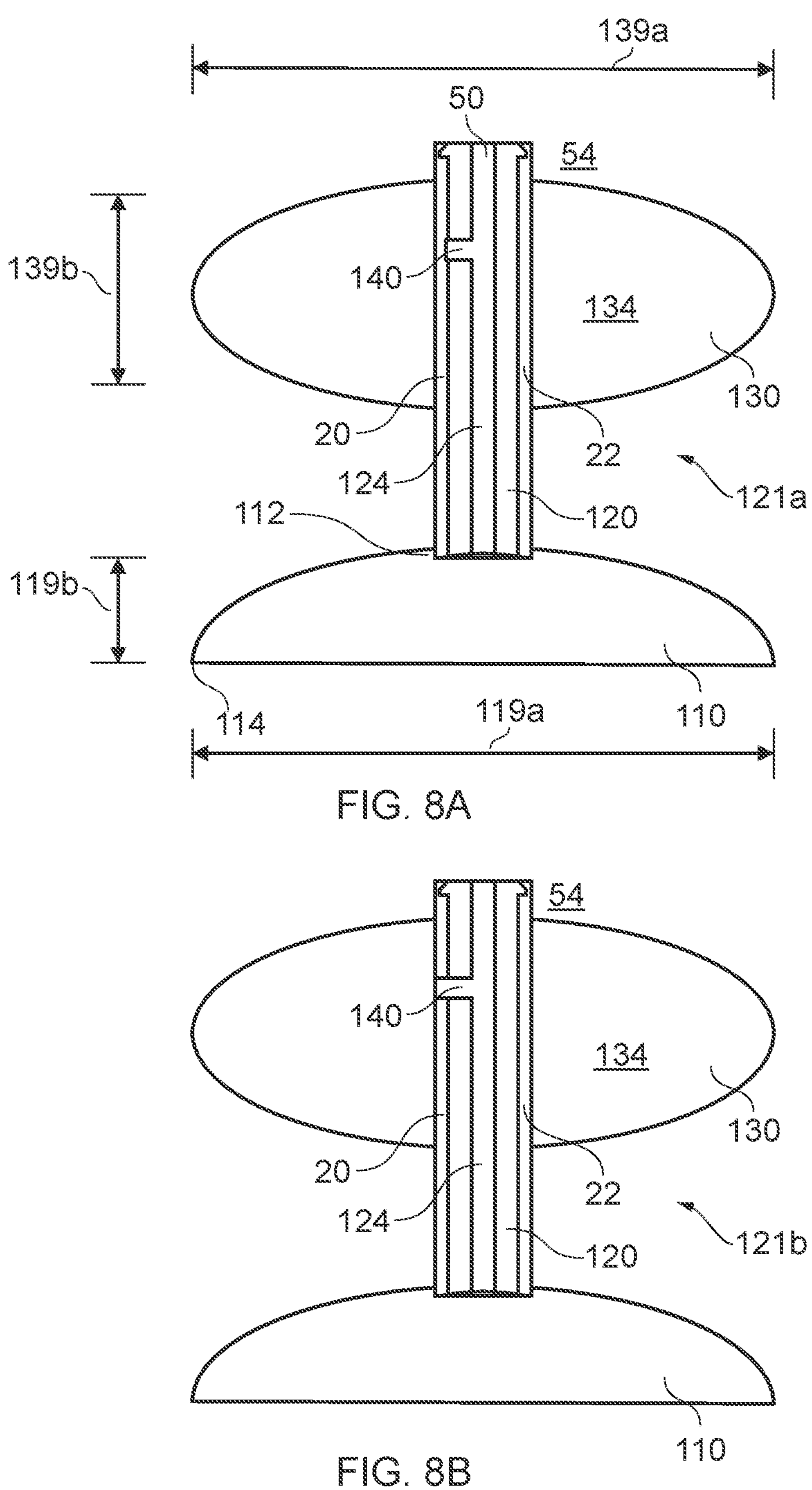
FIGS. 8A and 8B illustrate cross-sectional views of different aperture arrangements of the occlusion device.

The stem 120 has at least one aperture 140 in fluid communication with the internal volume 134 of the expandable member 130, and at least one aperture 150 at the distal end of the stem 120. However, the stem 120 may have any number or arrangement of apertures 140, 150 to insert fluid into the expandable member 130 and the internal volume 54 of the left atrial appendage respectively. FIGS. 8A and 8B show an exemplary cross-sectional view of the stem 120 that is moveable between a first position 121*a* and a second position 121*b*. FIGS. 8A and 8B show horizontal cross sections along line A-A of the stem 120 shown in FIG. 7C. In FIG. 8A, one aperture 140 extends from the central lumen 124 of the stem 120 and is in fluid communication with the internal volume 134 of the expandable member 130. Similarly, as shown in FIG. 7C, one distal aperture 150 is at the distal end 120*b* of the stem 120 and is in fluid communication with an internal volume 54 of the atrial appendage 50.

In some examples, the stem 120 may include a threaded engagement (not shown) that is operable by the medical practitioner to control the apertures 140, 150. The threaded engagement may be used to selectively occlude the aperture 140 or the distal aperture 150. The threaded engagement is operable by the medical practitioner so that the stem 120 is moveable between a first position 121*a* and a second position 121*b* to selectively occlude the aperture 140 or the distal aperture 150.

FIG. 8A shows the stem 120 in the first position 121*a*. In this position, the aperture 140 is occluded by the threaded engagement (not shown) and no longer in fluid communication with the internal volume 134 of the expandable member 130. The distal aperture 150 remains in fluid communication with the left atrial appendage 50. Therefore, when fluid 170 is introduced through the central lumen 124 of the stem 120, the fluid 170 is delivered through the distal aperture 150 and into the internal volume 54 of the left atrial appendage 50.

FIG. 8B shows the stem in the second position 121*b*. In the second position 121*b*, the aperture 140 remains in fluid communication with the internal volume 134 of the expandable member 130 while the distal aperture 150 is occluded by the threaded engagement (not shown) and no longer in fluid communication with the internal volume 54 of the left atrial appendage 50. Therefore, when fluid 170 is introduced through the central lumen 124 of the stem 120, the fluid 170 is delivered through the aperture 140 and into the internal volume 134 of the expandable member 130.

Figure 9A:
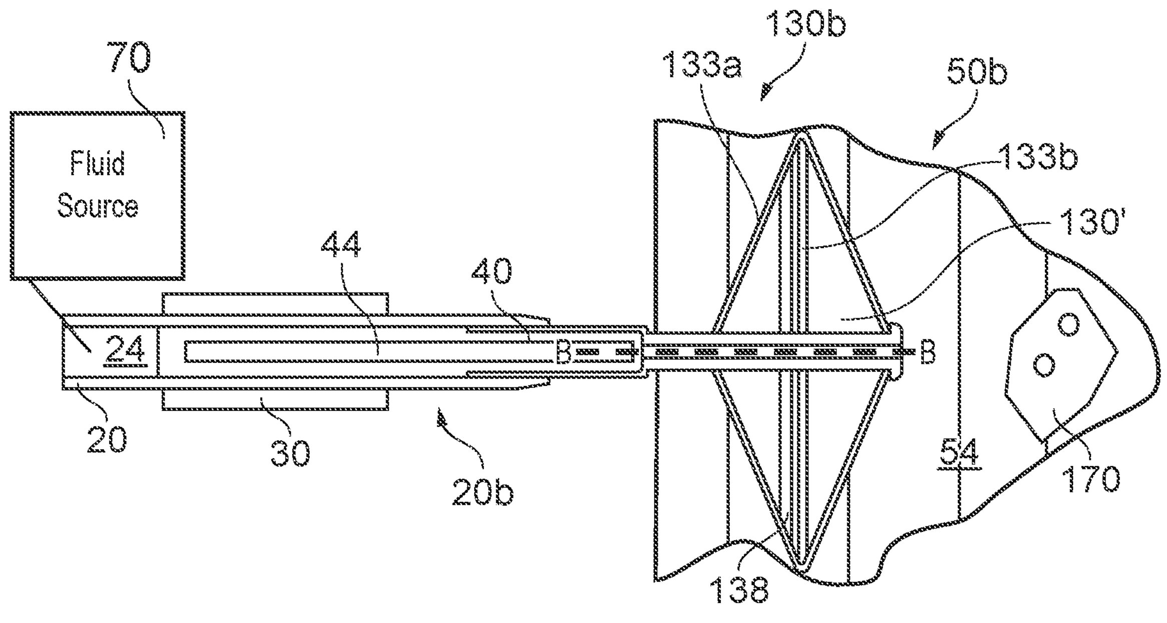
FIGS. 9A and 9B illustrate another embodiment of an exemplary occlusion assembly
Figure 9B:
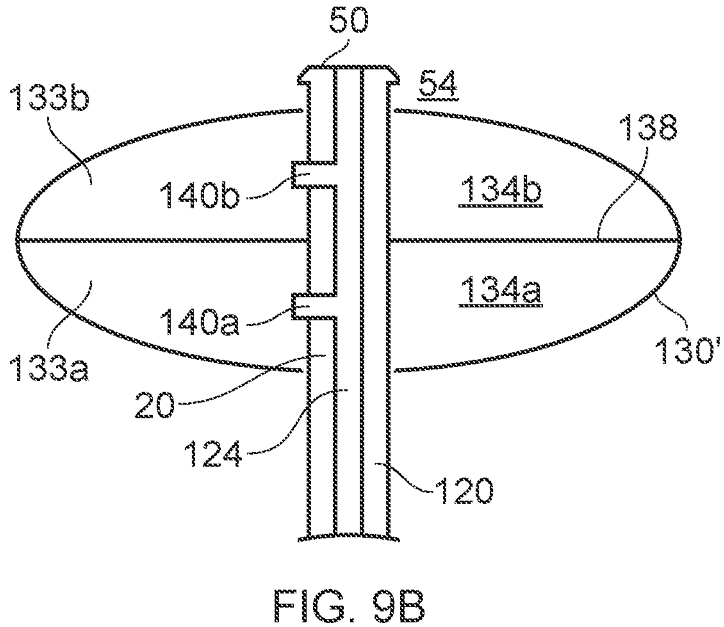

FIGS. 9A and 9B show another exemplary embodiment of the occlusion device 100. The proximal portion 110 is omitted from these figures for ease of clarity. In this embodiment, the expandable member 130' has a first internal chamber 133*a* and a second internal chamber 133*b* that are separated by a wall 138. The first chamber 133*a* has an internal volume 134*a* and the second chamber 133*b* has an internal volume 134*b*. In this example, the wall 138 extends along the width 139 of the expandable member 130, but it will be understood that the chambers 133*a*, 133*b* may be formed by placing the wall 138 along any orientation in the expandable member 130. Furthermore, any number of chambers 133*a*, 133*b* may be formed inside the expandable member 130 for better control of the sealing or filling of the occlusion device 100

FIG. 9B is a cross-sectional view of the stem 120 and the expandable member 130 along line B-B shown in FIG. 9A. In this example, the stem 120 has a first aperture 140*a* in fluid communication with the first internal chamber 133*a* and a second aperture 140*b* in fluid communication with the second internal chamber 133*b*. In this arrangement, each chamber is arranged to selectively expand with the introduction of fluid 170 into each internal volume 134*a*, 134*b* respectively. Similar to the stem 120 shown in FIGS. 8A and 8B, the stem 120 may include a dual step threaded engagement that is operable to occlude each aperture 140*a*, 140*b* independently. In this configuration, the threaded engagement may be activated between a first position and a second position (not shown) to selectively occlude each aperture 140*a*, 140*b* respectively. This enables the medical practitioner to selectively expand each chamber 134*a*, 134*b* of the expandable member 130. The expandable member 130' may therefore be selectively expanded depending on the shape of the internal volume 54 of the left atrial appendage 50. The expandable member 130' may there be adapted to occlude different shapes or sizes of the left atrial appendage 50.

Figure 10:
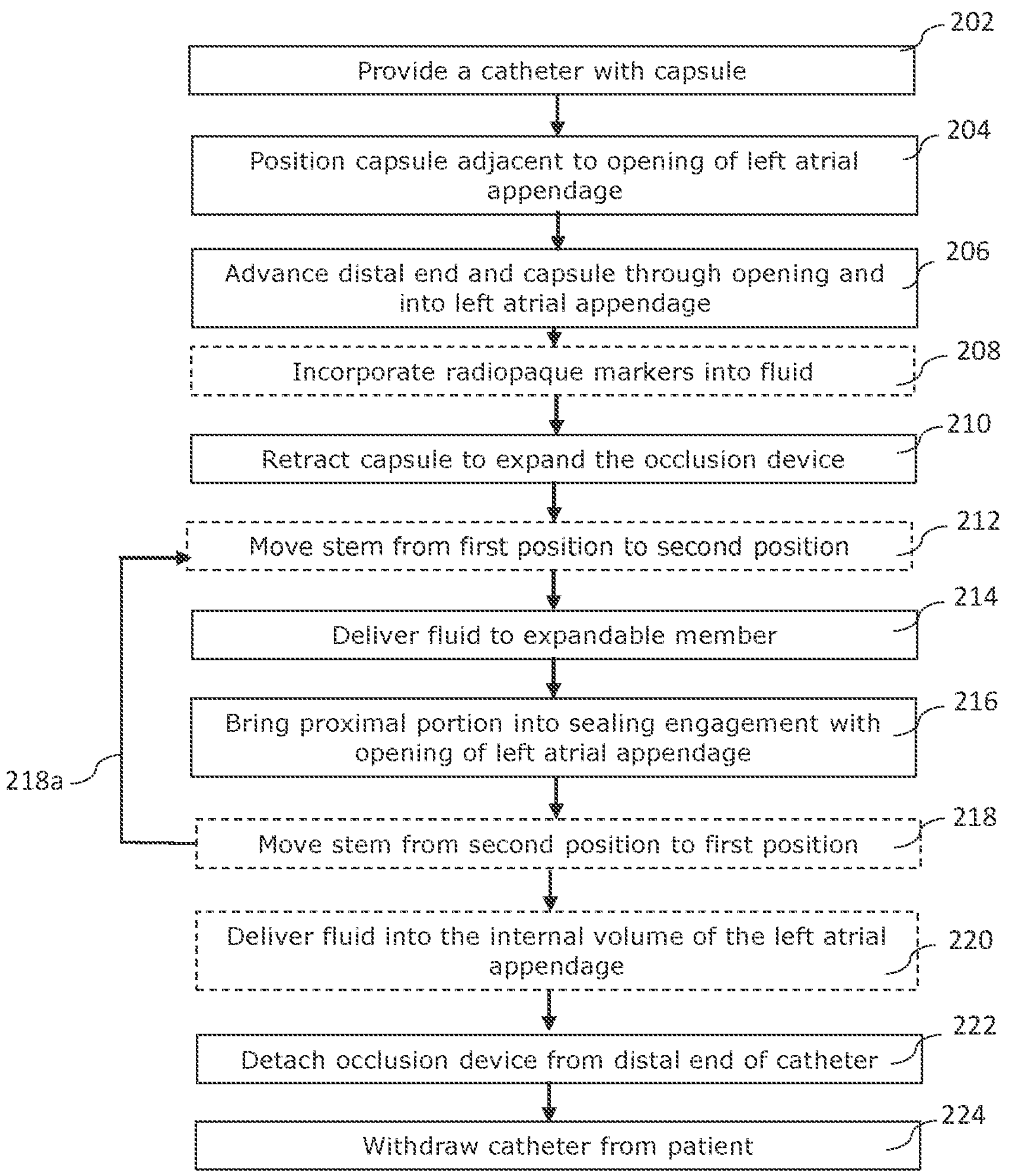
FIG. 10 illustrates an exemplary method of occluding a left atrial appendage.

An exemplary occlusion assembly 10 including an exemplary occlusion device 100 for occluding a left atrial appendage 50 is described above. An exemplary method for occluding the left atrial appendage is described below in relation to FIG. 10.

At step 202, an occlusion assembly 10 is provided with a catheter 20. The occlusion device 100 is loaded into a capsule 30 in a collapsed state 100*b* and is arranged on the distal end 20*b* of the catheter 20. The distal end 20*b* of the catheter 20 is positioned adjacent to the opening 52 of the left atrial appendage in step 204. As shown in FIG. 7B, the distal end 20*b* of the catheter 20 is advanced through the opening 52 towards the distal end 59*b* of the left atrial appendage 50 in step 206. As shown in FIG. 7D, the distal end of the catheter 20*b* is positioned inside the volume 54 of the left atrial appendage 50.

A fluid source 70 is connected to the catheter 20 and is arranged to deliver biogel 170 through the catheter 20 and into the occlusion device 100. Optionally, at step 208, radiopaque markers 170*a* may be incorporated into the biogel 170 before introducing the biogel 170 into the occlusion device 100.

The capsule 30 is then retracted proximally to move the occlusion device 100 from a collapsed state 100*a* to an expanded state 100*b* at step 210, as shown in FIG. 7C. In the expanded state 100*b*, the expandable member 130 is positioned inside the left atrial appendage 50.

Optionally, if the stem 120 has a plurality of apertures 140*a*, 140*b* and the stem 120 is arranged to be moveable between a first position 121*a* and a second position 121*b*, the stem is moved by the medical practitioner at step 121 to be in a second position 121*b*. In the second position 121*b*, at least one aperture 140 is in fluid communication with the internal volume 134 of the expandable member 130.

At step 214, biogel is delivered to the expandable member 130 with the fluid source 70. The expandable member 130 is at least partially expanded at step 214. The biogel 170 is delivered through the central lumen 24 of the catheter 20, through the central lumen 44 of the plunger 40, through the central stem 124 of the stem 120 and through at least one aperture 140 into the expandable member 130. The expandable member 130 expands to occlude the internal volume 54 of the left atrial appendage 50.

As the expandable member 130 expands at step 214, the proximal portion 110 of the occlusion device 100 is brought into sealing engagement with the opening 52 of the left atrial appendage 50 at step 216. The proximal portion 110 therefore seals the opening 52 of the left atrial appendage 50 from the left atrium LA.

Optionally, at step 218*a*, the stem 120 may be moved back into the first position 121*b* to occlude the aperture 140 before moving on to step 220. If the expandable member 130' has multiple apertures 140*a*, 140*b*, then the medical practitioner may return to step 212 to move the stem 120 back into a first position 121*a* to occlude the first aperture 140*a* so that the second chamber 133*a* may receive fluid through the second aperture 140*b* in step 214.

After the aperture 140 is in the first position 121*a* and is occluded, the medical practitioner may introduce biogel 170 into the internal volume 54 of the left atrial appendage 50 at step 220 through the distal aperture 150.

After the biogel 170 has been delivered inside to the expandable member 130 and optionally inside the left atrial appendage 50, the occlusion device 100 is detached from the distal end 20*b* of the catheter 20 at step 222. More specifically, the distal end 40*b* of the plunger 40 is detached from the proximal portion 110 by the use of a threaded engagement. Preferably, the distal end 40*b* of the plunger 40 is detached from the occlusion device 100 after the proximal portion 100 has created a seal against the opening 50 of the left atrial appendage. The distal end 20*b* of the catheter 20 (with the plunger 40) is then withdrawn from the patient at step 224.

With regard to the terms "distal" and "proximal" within this description, unless otherwise specified, the terms can reference a relative position of the portions of the delivery catheter system with reference to a medical practitioner and/or a location in the vasculature or heart. For example, "proximal" can refer to a position closer to the medical practitioner of the device or an incision into the vasculature, and "distal" can refer to a position that is more distant from the medical practitioner of the device or further from the incision along the vasculature (e.g., the end of the catheter).

Although the teachings have been described above with reference to one or more preferred embodiments, it will be appreciated that various changes or modifications may be made without departing from the scope as defined in the appended claims.

Where the word 'or' appears this is to be construed to mean 'and/or' such that items referred to are not necessarily mutually exclusive and may be used in any appropriate combination.

Although the invention has been described above with reference to one or more preferred embodiments, it will be appreciated that various changes or modifications may be made without departing from the scope of the invention as defined in the appended claims.

The invention claimed is:

1. An occlusion device for occluding a left atrial appendage, the device comprising:

a stem with an elongate tubular body and a central lumen that extends from a proximal end to a distal end;

a proximal portion arranged at the end of the stem, wherein the proximal portion is arranged to engage with an opening of the left atrial appendage; and an expandable member arranged at the distal end of the stem, the expandable member including a distal face, a proximal face, and an internal volume defined by the proximal face and the distal face;

wherein the central lumen of the stem is in fluid communication with the expandable member;

wherein the expandable member is arranged to be positioned inside a left atrial appendage; and wherein the expandable member is arranged to receive fluid into the internal volume such that the expandable member at least partially expands into contact with walls of the left atrial appendage and displaces the proximal portion in a direction towards the expandable member.

2. The occlusion device of claim 1, wherein the expandable member is asymmetric, having a width greater than its height.

3. The occlusion device of claim 2, wherein the width of the expandable member is substantially oval or elliptical shaped.

4. The occlusion device of claim 1, wherein the expandable member comprises a nitinol mesh.

5. An occlusion device for occluding a left atrial appendage, the device comprising:

a stem with an elongate tubular body and a central lumen that extends from a proximal end to a distal end;

a proximal portion arranged at the end of the stem, wherein the proximal portion is arranged to engage with an opening of the left atrial appendage; and an expandable member arranged at the distal end of the stem;

wherein the central lumen of the stem is in fluid communication with the expandable member;

wherein the expandable member is arranged to be positioned inside a left atrial appendage;

wherein the expandable member is operable to at least partially expand and displaces the proximal portion in a direction towards the expandable member; and wherein the distal end of the stem extends through the expandable member and is secured to an outer surface at a distal end of the expandable member.

6. The occlusion device of claim 1, wherein the stem is in fluid communication with the expandable member through at least one aperture extending from the central lumen of the stem.

7. The occlusion device of claim 6, wherein the aperture extends perpendicularly from the central lumen.

8. The occlusion device of claim 7, wherein the stem is arranged to be positioned in a distal end of a catheter so that the distal end of the catheter extends around the stem, wherein the stem is moveable between a first position and a second position, wherein in the first position, the at least one aperture is occluded and no longer in fluid communication with the expandable member, and in a second position, the at least one aperture is in fluid communication with the expandable member.

9. The occlusion device of claim 6, wherein the stem further comprises at least one aperture at the distal end of the stem, wherein the at least one aperture is arranged to be in fluid communication with the left atrial appendage.

10. An occlusion device for occluding a left atrial appendage, the device comprising:

a stem with an elongate tubular body and a central lumen that extends from a proximal end to a distal end;

a proximal portion arranged at the end of the stem, wherein the proximal portion is arranged to engage with an opening of the left atrial appendage; and an expandable member arranged at the distal end of the stem;

wherein the central lumen of the stem is in fluid communication with the expandable member;

wherein the expandable member is arranged to be positioned inside a left atrial appendage;

wherein the expandable member is operable to at least partially expand and displace the proximal portion in a direction towards the expandable member; and wherein the expandable member comprises at least two chambers.

11. The occlusion device of claim 10, wherein the stem is in fluid communication with each chamber through at least one respective aperture so that each chamber is arranged to be expanded separately.

12. The occlusion device of claim 1, wherein the proximal portion is dome shaped and an apex of the dome is proximal to the expandable member.

13. The occlusion device of claim 1, wherein the proximal portion comprises a bioinert polymer.

14. The occlusion device of claim 1, wherein the proximal portion is at least partially coated with a material coating.

15. An occlusion assembly for occluding a left atrial appendage, the assembly comprising:

a catheter with an elongate tubular body and a central lumen that extends from a proximal end to a distal end of the catheter, the distal end arranged to be positioned at an opening of the left atrial appendage, the distal end including a capsule;

a fluid source coupled to the catheter; and an occlusion device comprising:

a stem with an elongate tubular body and a central lumen that extends from a proximal end to a distal end;

a proximal portion arranged at the proximal end of the stem, wherein the proximal portion is arranged to engage with an opening of the left atrial appendage; and an expandable member arranged at the distal end of the stem, the expandable member comprising a frame and an internal volume defined by the frame;

wherein the capsule is configured to maintain the occlusion device in a radially collapsed state;

wherein the frame is at least partially self-expanding such that releasing the expandable member from the capsule causes the expandable member to at least partially expand;

wherein the central lumen of the stem is in fluid communication with the expandable member to deliver fluid from the fluid source to the internal volume and the expandable member is arranged to be positioned inside a left atrial appendage; and wherein the expandable member is operable to receive fluid from the fluid source into the internal volume to further expand and to displace the proximal portion in a direction towards the expandable member, wherein the occlusion device is releasably connected to the distal end of the catheter.

16. The occlusion device of claim 6, wherein when the stem of the occlusion device further comprises at least one aperture at the distal end of the stem and wherein the at least one aperture is arranged to be in fluid communication with the left atrial appendage, and wherein the fluid source is further operable to deliver fluid into the left atrial appendage.

17. The occlusion assembly according to claim 15, wherein the occlusion assembly further comprises a plunger with a proximal end and a distal end, wherein the proximal end of the plunger is housed in the distal end of the catheter and the distal end of the plunger is releasably connected to the proximal portion of the occlusion device, so that the occlusion device is releasably connected to the catheter through the plunger.

18. The occlusion assembly according to claim 15, wherein the fluid is one of: biogel, saline or contrast media.

* * * * *